United States Patent
Schlumpberger et al.

(10) Patent No.: US 10,329,553 B2
(45) Date of Patent: Jun. 25, 2019

(54) METHOD FOR ISOLATING RNA INCLUDING SMALL RNA WITH HIGH YIELD

(71) Applicant: QIAGEN GmbH, Hilden (DE)

(72) Inventors: Martin Schlumpberger, Hilden (DE); Stefanie Schröer, Hilden (DE); Vera Holländer, Unna (DE)

(73) Assignee: QIAGEN GmbH, Hilden (DE)

( * ) Notice: Subject to any disclaimer, the term of this patent is extended or adjusted under 35 U.S.C. 154(b) by 116 days.

(21) Appl. No.: 14/425,252

(22) PCT Filed: Sep. 3, 2013

(86) PCT No.: PCT/EP2013/068197
§ 371 (c)(1),
(2) Date: Mar. 2, 2015

(87) PCT Pub. No.: WO2014/033326
PCT Pub. Date: Mar. 6, 2014

(65) Prior Publication Data
US 2015/0232831 A1 Aug. 20, 2015

Related U.S. Application Data

(60) Provisional application No. 61/696,244, filed on Sep. 3, 2012.

(30) Foreign Application Priority Data

Sep. 3, 2012 (EP) ..................................... 12182741

(51) Int. Cl.
*C12N 15/10* (2006.01)
*C07H 21/02* (2006.01)

(52) U.S. Cl.
CPC ......... *C12N 15/1006* (2013.01); *C07H 21/02* (2013.01); *C12N 15/1013* (2013.01)

(58) Field of Classification Search
None
See application file for complete search history.

(56) References Cited

U.S. PATENT DOCUMENTS

| | | | | |
|---|---|---|---|---|
| 6,379,710 B1* | 4/2002 | Badylak | ............... | A61K 35/407 424/553 |
| 7,871,764 B1* | 1/2011 | Bavykin | ............... | C12Q 1/6806 435/4 |
| 2004/0014703 A1* | 1/2004 | Hollnder | ............... | C07C 211/62 514/44 R |
| 2005/0026159 A1* | 2/2005 | Robbins | ............. | C12N 15/1006 435/6.13 |
| 2005/0054847 A1* | 3/2005 | Madden | ................ | C12N 15/111 536/25.4 |
| 2005/0118570 A1* | 6/2005 | Hollis | .................. | C12Q 1/6806 435/5 |

FOREIGN PATENT DOCUMENTS

| | | |
|---|---|---|
| EP | 0 343 934 A2 | 11/1989 |
| EP | 1 260 595 A2 | 11/2002 |
| EP | 0 880 537 B1 | 12/2004 |
| EP | 1 693 453 A1 | 8/2006 |
| WO | 95/21849 A1 | 8/1995 |
| WO | 96/41811 A1 | 12/1996 |
| WO | 98/31461 A1 | 7/1998 |
| WO | 98/31840 A1 | 7/1998 |
| WO | 01/71732 A2 | 9/2001 |
| WO | 03/004150 A1 | 1/2003 |
| WO | 2004/003231 A2 | 1/2004 |
| WO | 2005/012523 A1 | 2/2005 |
| WO | 2005/054466 A2 | 6/2005 |
| WO | 2009/016110 A1 | 2/2009 |
| WO | 2011/104032 A1 | 9/2011 |
| WO | 2012/028737 A1 | 3/2012 |

OTHER PUBLICATIONS

Ambion—RNA, "mirVana™ miRNA Isolation Kit," Internet Citation, http://tools.invitrogen.com/content/sfs/manuals/cms_055423 (33 pages) (Jan. 1, 2011).
Chomczynski et al., "Single-Step Method of RNA Isolation by Acid Guanidinium Thiocyanate-Phenol-Chloroform Extraction," *Analytical Biochemistry* 162:156-159 (1987).
Genov et al., "Stability of subtilisins and related proteinases (subtilases)," *Int. J. Peptide Protein Res.* 45:391-400 (1995).
Norgen, "microRNA Purification Kit," Product #21300, Internet Citation, http://www.norgenbiotek.com/product_resources/microrna_purification_kit_microrna_purification_kit_protocol_21300_946 (14 pages) (Jan. 1, 2009).
QIAGEN Supplementary Protocol: Purification of miRNA from animal cells using the RNeasy® Plus Mini Kit and RNeasy MinElute® Cleanup Kit, Internet Citation http://www1.qiagen.com/literature/render.aspx?id=577 (5 pages) (Jun. 2006).

* cited by examiner

*Primary Examiner* — Robert T. Crow
(74) *Attorney, Agent, or Firm* — Seed IP Law Group LLP

(57) ABSTRACT

The present invention provides a method for isolating RNA including small RNA having a size of 200 nt or less from a sample, comprising the following steps: a) providing a composition comprising RNA and a chaotropic agent; b) adding alcohol; c) incubating the mixture for at least 2 min; d) adding additional alcohol to the mixture to adjust the overall alcohol concentration in the mixture to ≥50%; e) binding RNA contained in the mixture to a nucleic acid binding solid phase; f) optionally washing the bound RNA; g) optionally eluting RNA from the solid phase. Due to the step-wise addition of alcohol, the overall RNA yield and the yield of small RNA is improved.

27 Claims, 16 Drawing Sheets a)

b)

c)

a)

b)

a)

b)

a)

b)

a)

b)

a)

b)

METHOD FOR ISOLATING RNA INCLUDING SMALL RNA WITH HIGH YIELD

The present invention pertains to a method for isolating RNA including small RNA from a sample and in particular provides means for efficiently isolating total RNA, including small RNA with high yield from various samples.

The study of small nucleic acids in the order of 500 nucleotides or less from various tissues, body fluids and other biological samples is an area of extreme interest and promises to remain one for the future. Small nucleic acids in particular include but are not limited to small RNAs such as inter alia micro RNAs (miRNA) and small interfering RNA molecules both of which can have a powerful effect on the expression of a gene. Furthermore, also other small nuclear and small nucleolar RNAs (e.g. snRNAs and snoRNAs) involved in mRNA and rRNA processing are of interest. Furthermore, nucleic acids such as RNA having a length of 500 nucleotides or less are also often contained as degradation products in other samples and must be efficiently captured therefrom. With the increasing interest in respective small RNAs, the standard isolation procedures have been modified to facilitate the isolation of small nucleic acids and in particular to improve the yield of small nucleic acids. This as known protocols used as standard to isolate total RNA are usually not ideal for isolating small RNAs because small RNA is often not effectively captured and eluted during the isolation process using standard methods. Therefore, total RNA isolated using standard procedures usually does not comprise small RNA in sufficient amounts and thus do not provide acceptable yields because small RNAs are either not bound or get lost during the nucleic acid isolation procedure. Thus, there is a need for improved techniques for the efficient isolation of total RNA, which includes the desired small RNAs.

Methods that have been optimized for the isolation of small RNA often rely on phenol/chloroform extraction and subsequent alcohol fractionation. Phenol/chloroform-based organic extraction methods are often performed according to the Chomczynski method (Chomczynski and Sacchi, 1987: Single-step method of RNA isolation by acid guanidinium thiocyanate-phenol-chloroform extraction. Anal. Biochem. (162): 156-159). According to said methods, the RNA is concentrated in the aqueous phase during phenol/chloroform extraction and is then subsequently isolated therefrom e.g. by adding alcohol and binding the RNA to a nucleic acid binding solid phase. In said binding step, special conditions are again required to efficiently capture the small RNAs in the isolated total RNA. A commercial kit that is based on a respective phenol/chloroform method is the MirVana miRNA isolation kit (Ambion). After phenol/chloroform extraction, the protocol follows a fractionation strategy, wherein larger RNAs (more than 200 nucleotides) are bound in a first binding step to nucleic acid binding solid phase at moderate alcohol concentrations (typically 30-40%). The flow-through comprises the small RNAs. Said small RNAs are captured from the flow-through by a second binding step by raising the alcohol concentration to more than 50% (typically 55-70%) and binding the small RNA to a second solid phase. This protocol is inconvenient as two different binding conditions and two different nucleic acid binding solid phases are required. Furthermore, a protocol is provided with the MirVana miRNA isolation kit wherein total RNA including small RNA is isolated from the aqueous phase obtained after the phenol/chloroform extraction. Here, the binding conditions are established by increasing the alcohol concentration to the required amounts (typically 55-70%) in one step. Respective methods are also described in WO 2005/012523 and WO 2005/054466. However, also in these protocols an organic phenol/chloroform extraction step is performed in advance. Another phenol/chloroform based commercial product is the miRNAeasy Mini kit (QIAGEN). It provides high quality and high yields of total RNA including small RNA from various different biological samples.

However, such methods that require an organic extraction step such as in particular a phenol/chloroform extraction have drawbacks because phenol is a toxic agent. There is a great demand for phenol-free RNA isolation methods which allow to isolate total RNA including small RNA from various samples with high yield and quality.

Phenol-free methods for isolating RNA including small RNAs are also known in the prior art. To allow binding of total RNA including small RNA to a nucleic acid binding solid phase chaotropic agents and high concentrations of alcohol are used. Usually, the nucleic acid binding solid phases used comprise or consist of silica. However, the recovery of small RNA species like miRNA in methods that are based on binding the RNA to silica surfaces in the presence of alcohol and chaotropic substances require very high alcohol concentrations. Usually, approximately at least 50% alcohol is used in the binding mixture, usual ranges include 50-80% (v/v) alcohol in the binding mixture. However, when using respective protocols (which do not involve a phenol based organic extraction step) that involve high alcohol concentrations to allow binding of the small RNA, the total RNA yield and also the obtained small RNA yield is often reduced. With certain biological samples such as e.g. fibrous tissue samples (e.g. heart or muscle sample), the RNA isolation is particular challenging. Thus, generally, the performance of these protocols is unfortunately not comparable with phenol/chloroform based isolation methods. The problems are encountered irrespective of what type of nucleic acid binding solid phase is used. These problems are observed with column based methods as well as with methods that involve the use of magnetic particles.

It is the object of the present invention to provide a method for isolating total RNA including small RNA which overcomes at least one of the above disadvantages of the prior art methods. In particular, it was the object of the present invention to provide a method for isolating total RNA including small RNA which avoids the use of phenol and provides good RNA yields, in particular good small RNA yields, with different sample types, including fibrous tissues.

SUMMARY OF THE INVENTION

The inventors have found that the recovery of small RNA in a total RNA preparation and also the overall RNA yield can be significantly improved, if the alcohol that is needed to adjust the conditions for binding small RNA to a nucleic acid binding phase is added in a step-wise manner. As is shown by the examples, an increase in the total RNA yield of up to 4-fold was observed when adding the alcohol in a step-wise manner. Furthermore, the small RNA yield was also significantly improved. This was a highly unexpected finding as so far it was assumed that only the overall alcohol concentration in the binding mixture is decisive for efficiently binding and thus isolating small RNA. However, the inventors have found that the small RNA yield as well as the overall total RNA yield can be significantly improved, if the same alcohol concentrations and binding conditions known in the prior art are used, if, however, the alcohol is added in a step-wise manner instead of adding it in one step.

The molecular mechanisms underlying these significant improvements are not understood.

Without wishing to be bound by theory, it could be that adjusting the alcohol concentration to ≥50% in just one step results in an immediate precipitation of RNA, with individual aggregates of RNA growing too large too quickly for productive interaction with and binding to the solid phase. Additionally, if no phenol-based organic extraction step is performed in advance (e.g. no phenol/chloroform extraction), adjusting the high alcohol concentration in just one step may dramatically reduce the solubility of contaminants, in particular proteins. Thereby, the RNA binding capacity of the nucleic acid binding phase could be reduced, thereby reducing the overall yield of the isolated RNA. It could be that these problems are avoided when following the teachings of the present invention. However, the molecular rationale underlying the present invention is not decisive. The achieved improvements are demonstrated with different nucleic acid binding solid phases and various tissues. According to a first aspect, a method is provided for isolating RNA including small RNA having a length of 300 nt or less, preferably 200 nt or less from a sample, comprising the following steps:

a) providing a composition comprising RNA and a chaotropic agent;
b) adding alcohol;
c) incubating the mixture for at least 2 min;
d) adding additional alcohol to the mixture to adjust the overall alcohol concentration in the mixture to ≥50%;
e) binding RNA contained in the mixture to a nucleic acid binding solid phase, wherein after step e), RNA including small RNA is bound to the solid phase;
f) optionally washing the bound RNA;
g) optionally eluting RNA from the solid phase.

The examples show that the present invention provides a highly efficient method for isolating total RNA, including small RNA such as miRNA, from various samples including samples from which it is particularly difficult to isolate RNA with good yields using methods that do not comprise a phenol-based extraction step. The method according to the present invention which does not require the use of phenol or other organic extraction agents provides similar results and RNA yields as prior art methods, which use phenol for isolating the RNA. By providing a method which provides comparable RNA yields while avoiding the use of phenol, the present invention provides a major contribution to the prior art and significantly improves existing phenol-free RNA isolation methods. Furthermore, the RNA isolation method according to the present invention can be easily implemented in existing protocols which either aim at the isolation of total RNA including small RNA or which aim at the parallel isolation of total RNA, including small RNA, and DNA from various samples.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

FIG. 7—heart; FIG. 8—liver) following different isolation protocols (see example 3). Shown are pictures obtained after gel electrophoresis of an aliquot of the isolated RNA.

DETAILED DESCRIPTION OF THE INVENTION

Figure 1:
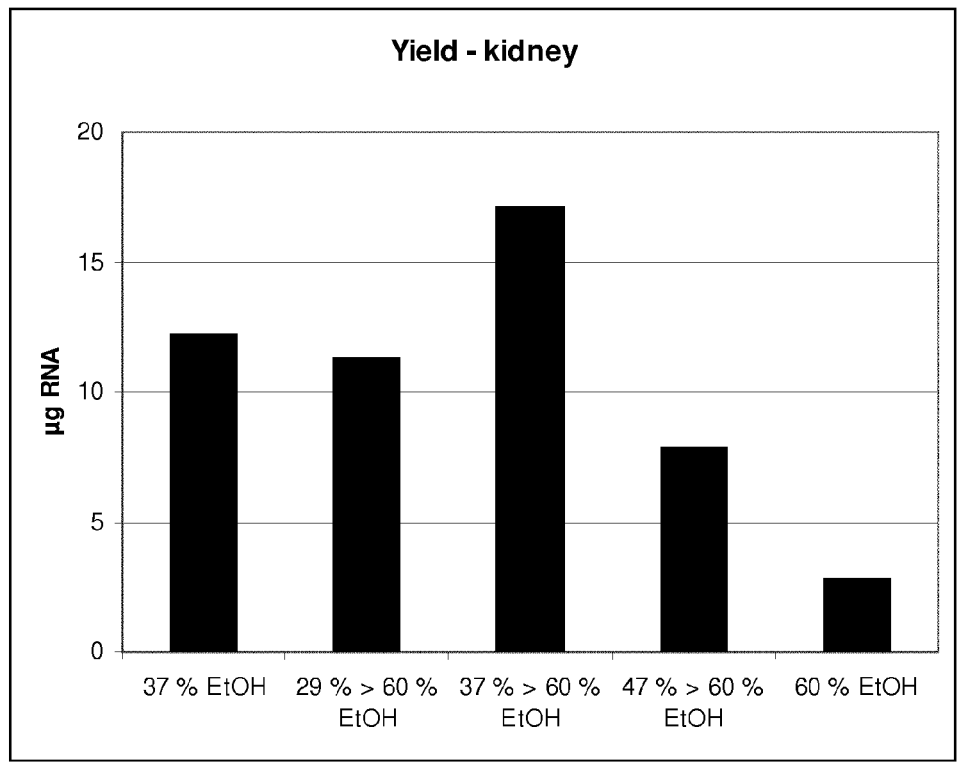
FIG. 1: Shows the RNA yield obtained with kidney tissue following either prior art approaches or the step-wise addition of alcohol according to the principle of the invention (see example 1).

The present invention provides an improved method for isolating RNA including small RNA having a length of 200 nt or less from a sample. The method comprises the following steps:
- a) providing a composition comprising RNA and a chaotropic agent;
- b) adding alcohol, thereby providing a mixture comprising RNA, a chaotropic salt and alcohol;
- c) incubating the mixture for at least 2 min, wherein during said incubation step preferably a proteolytic digest is performed;
- d) adding additional alcohol to the mixture to adjust the overall alcohol concentration in the mixture to ≥50%, preferably ≥55%, more preferred ≥60%;
- e) binding small RNA contained in the mixture to a nucleic acid binding solid phase, wherein after step e), RNA including small RNA is bound to the solid phase;
- f) optionally washing the bound RNA;
- g) optionally eluting RNA from the solid phase.

As is shown by the examples, the step-wise addition of the alcohol that is required to establish the binding conditions to efficiently capture RNA including small RNA surprisingly results in a significantly improved total RNA yield, including an improved small RNA yield. The remarkable effects are observed when isolating RNA from various biological samples, including complex samples such as fibrous tissue samples and blood. Following a step-wise approach as taught herein results in overall RNA yields that are increased up to 4-fold and more compared to identical protocols wherein no step-wise approach is followed. Furthermore, the examples also show that the small RNA yield is likewise increased if following a step-wise approach when adjusting the high alcohol concentrations for small RNA binding. Furthermore, as is shown by the examples, the method according to the present invention achieves these results with numerous sample types, including various tissue samples, including fibrous tissue samples. This broad applicability of the method is advantageous as it allows the user to conveniently use one RNA isolation protocol for isolating total RNA, including small RNA, from various different samples. From the above it is evident that the present invention makes a significant contribution to the prior art.

Subsequently, we will explain each step and preferred embodiments thereof in detail.

The RNA isolation procedure starts with step a), wherein a composition comprising RNA and a chaotropic agent is provided. For providing said composition, several options exist which will also be explained in detail subsequently. Usually, said composition will be a lysate which was obtained by lysing a biological sample, such as e.g. a cell or tissue sample. Suitable lysis procedures are known in the prior art and lysis procedures are also described below. Said lysate may have been further processed prior to step a). Suitable processing steps include but are not limited to clearing the lysate or removing DNA from the lysate. In any case, a composition comprising RNA and a chaotropic agent is provided in step a) and the RNA is then isolated from said composition performing the steps described herein.

A chaotropic agent causes disorder in a protein or nucleic acid by, for example, but not limited to altering the secondary, tertiary or quaternary structure of a protein or a nucleic acid while leaving the primary structure intact. Preferably, the chaotropic agent comprised in the composition that is provided in step a) is a chaotropic salt such as a guanidinium salt. Preferred chaotropic agents include but are not limited to guanidinium hydrochloride, guanidinium thiocyanate (GTC), guanidinium isothiocyanate (GITC), sodium thiocyanate, sodium iodide, sodium perchlorate, sodium trichloroacetate, sodium trifluroacetate, urea and the like. Preferably, the chaotropic agent is GTC or GITC or an equally strong chaotropic agent. Respective strong chaotropic agents are advantageous as they may efficiently protect the RNA comprised in the composition from enzymatic degradation. Furthermore, the chaotropic agent contributes to establish the RNA binding conditions (see in particular step e) below). The chaotropic agent may have been introduced during lysis, as the use of chaotropic agents for lysis is preferred. According to one embodiment, the composition provided in step a) comprises a chaotropic agent, preferably a chaotropic salt, in a concentration selected from the group consisting of 0.5 M to saturation, 0.75M to 5M, 1 M to 4.5M, 1.25M to 4.25M, 1.5M to 4M, 1.75 to 3.75M and 2M to 3.5M. Most preferred is a concentration of 2.75 to 3.75 if a chaotropic salt such as GTC or GITC is used.

In step b) alcohol is added. The alcohol that is added in step b) assists to prepare the binding conditions for binding step e). It is preferred to use an aliphatic, short chained branched or unbranched alcohol with preferably one to 5 carbon atoms. Examples are methanol, ethanol, propanol, isopropanol and butanol. Also mixtures of alcohols can be added in step b). The alcohol is preferably selected from isopropanol and ethanol, particularly well suitable is ethanol. Respective alcohols are also added in the prior art to adjust RNA binding conditions that allow to also capture small RNA. However, in contrast to the prior art methods, not the full amount of alcohol required for adjusting binding conditions that allow to bind RNA including small RNA to a nucleic acid binding solid phase (approx. at least 50% (v/v); preferably at least 60% (v/v))) is added in step b). Conversely, only a portion of the required overall amount of alcohol is added in step b). The portion of alcohol added in step b) usually corresponds to approx. 40% to 80% of the overall alcohol concentration that is added for small RNA binding in step e). Thus, if the final alcohol concentration used for binding in step e) is 60% (v/v), alcohol is added in step b) in an amount so that it is comprised in the resulting mixture in a concentration of approx. 25% (v/v) (corresponds to approx. 41% of the final alcohol concentration) to 47% (v/v) (corresponds to approx. 78% of the final alcohol concentration). Preferably, the portion of alcohol added in step b) corresponds to approx. 45% to 75%, 50% to 70%, 55% to 65%, 57% to 64%, 58% to 63% and most preferably 59% to 62% of the overall, i.e. final alcohol concentration that is established for small RNA binding in step e).

According to one embodiment the alcohol is added in step b) in an amount so that it is comprised in the resulting mixture in a concentration of at least 25% (v/v), preferably at least 30% (v/v), more preferably at least 35% (v/v). However, it is preferred that the alcohol concentration in the mixture does not exceed 48% (v/v) alcohol if the overall alcohol concentration that is established in step d) is at least 60% (v/v). It is preferred to add an amount of alcohol in step b) so that the resulting mixture comprises the alcohol in a concentration that lies in a range selected from 25% (v/v) to 45% (v/v), preferably 27.5% (v/v) to 42.5% (v/v), more preferred 30% to 40% (v/v), most preferred 32.5% to 38% (v/v). These amounts are particularly suitable if the final alcohol concentration for binding in step e) is approx. 60% (v/v).

In step c), the obtained mixture is incubated for at least 2 minutes, preferably at least 3 min, at least 4 min, at least 5 min, at least 7 min and more preferred at least 10 min. A respective incubation step is important to ensure that the alcohol is indeed added step-wise and accordingly, to ensure high total RNA and in particular high small RNA recovery. The mixture can be agitated during incubation (see also below).

According to a preferred embodiment, a proteolytic digest using a proteolytic enzyme is performed in incubation step c). Performing a proteolytic digest in step c) improves the RNA isolation with respect to yield and purity, in particular if difficult or complex samples such as fibrous tissue or blood are processed. It is assumed that the stepwise addition of alcohol as taught herein has particular advantages when being combined with a proteolytic digest wherein a proteolytic enzyme such as proteinase K is used. The digestion with proteinase K at moderately high concentrations of chaotropic salt (comprised in the RNA containing composition provided in step a)) and intermediate concentrations of alcohol (provided due to step b)) is significantly more efficient compared to both high chaotrop concentration and no alcohol (such as e.g. ethanol) and lower chaotrop concentration and high alcohol concentrations. The proteolytic enzyme digests proteins. This is an advantage because proteins could precipitate at the higher alcohol concentrations that are adjusted in step d) and thereby could reduce RNA binding to the solid phase. Furthermore, the proteolytic digest supports the digestion of difficult samples such as fibrous tissue samples.

A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K.

The proteolytic enzyme can be added either prior to, during or after step b). These embodiments are feasible for many biological samples. It is preferred though to add the proteolytic enzyme prior to adding the alcohol in step b). The inventors found that for specific samples, such as e.g. muscle tissue, it is decisive to add the proteolytic enzyme before adding the alcohol in step b) as otherwise, RNA cannot be purified efficiently. For other sample types it makes no difference whether the alcohol or the proteolytic enzyme is added first. However, to ensure that the method is universally applicable, it is preferred to add the proteolytic enzyme prior to step b) and accordingly, add the proteolytic enzyme prior to adding the alcohol according to step b). In either case, the proteolytic digest occurs in incubation step c) in the presence of alcohol and a chaotropic agent. It was found that the digest using a proteolytic enzyme is most efficient if the proteolytic digest is performed in the presence of a chaotropic salt and alcohol.

As is shown by the examples, in step c), different incubation times are suitable for various samples that can be processed according to the teachings of the present invention. On average, incubation times between 3 and 15 minutes were sufficient for achieving high RNA yields. Thus, preferably, incubation occurs for at least 2.5 minutes, at least 3 minutes, preferably at least 5 minutes, more preferably at least 7.5 minutes or most preferably at least 10 minutes. As is shown by the examples, longer incubation times are not necessary as this does not further increase the RNA yield. This is advantageous considering the necessary time for performing the protocol. However, if desired also longer incubation times can be used. As discussed above, it is preferred to add a proteolytic enzyme prior to step b) in order to perform a proteolytic digest in step c). During incubation step c) the proteolytic enzyme is active and accordingly can digest proteins comprised in the mixture. It was found that incorporating a respective proteolytic digestion step results in significantly increased RNA yields. The digestion can be assisted by heating or agitation. In the prior art, a digest with a proteolytic enzyme such as proteinase K is often performed at elevated temperatures of for example at least 50° C. or even at least 55° C. However, such heating steps are often inconvenient, as special laboratory equipment is required. Furthermore, many automated systems do not comprise a heating unit. Here, it was surprisingly found by the inventors that using the conditions specified herein, wherein the proteolytic digest is performed in the presence of a chaotropic salt and alcohol, allows to perform the proteolytic digest at lower temperatures and even at room temperature. Therefore, it is preferred that incubation step c) occurs at a temperature of 45° C. or less, 40° C. or less, 37° C. or less or 30° C. or less. Preferably, no heating step is performed and incubation step c) is carried out at a temperature between 15° C. and 30° C. and accordingly at room temperature. Performing incubation step c) at room temperature is very convenient and furthermore, surprisingly has the advantageous effect that the RNA is even less degraded compared to methods which use a common heating step during proteolytic digestion.

Incubation step c) may be performed while agitating the mixture. However, agitation is not necessary. Non-limiting examples of agitation include shaking, stirring, mixing, vibrating or by vertically moving a plunger, e.g. of a robotic system that can be used to process magnetic beads. In certain aspects, agitation comprises shaking. The shaking can be one, two, or three dimensional shaking. Agitating can be performed for example in a mixer with at least 50 rpm, at least 100 rpm, at least 200 rpm, at least 500 rpm or at least 1,400 rpm. When using at least one proteolytic enzyme, incubation conditions are used that ensure that said enzyme works efficiently and is catalytically active. Preferably, the incubation is performed in the presence of salts and/or ions that promote and/or maintain the activity of the proteolytic enzyme. As a chaotropic agent such as a chaotropic salt is comprised in the mixture and the enzyme is very active under these conditions, it is usually not necessary to add further salts. However, further salts or other additives can be added if desired. Suitable salts include but are not limited to NaCl, KCl, $MgCl_2$, or $CaCl_2$ or chaotropic agents such as chaotropic salts. The above described conditions are particularly favourable when using a proteolytic enzyme such as proteinase K and said conditions promote the digestion and increase the overall RNA yield.

Therefore, according to one embodiment, the mixture that is obtained after adding alcohol in step b) comprises:
 RNA;
 at least one chaotropic salt;

alcohol, preferably isopropanol or ethanol, in a concentration between 25% to 42.5% (v/v), preferably 30% to 40% (v/v), more preferred 32.5% to 38% (v/v).

According to a preferred embodiment, the mixture obtained after adding the alcohol in step b) and which accordingly is incubated in subsequent step c), comprises:
RNA;
a chaotropic salt in a concentration selected from 0.5M to 5 M, 0.75 to 4M, 1 to 3.5 M, 1.25M to 3.25M, 1.5M to 3M, 1.75 to 2.75M and 1.75 M to 2.5 M;
a proteolytic enzyme, preferably proteinase K;
alcohol, preferably isapropanol or ethanol, in a concentration between 25% to 42.5% (v/v), preferably 30% to 40% (v/v), more preferred 32.5% to 38% (v/v).

As described above, it is preferred to add the proteolytic enzyme prior to step b). However, it may also be added subsequent to adding the alcohol in step b). In non-limiting aspects, the proteolytic enzyme is comprised in said mixture that is incubated in step c) in a concentration of at least 12 mAU, at least 20 mAU, at least 25 mAU or at least 30 mAU. Suitable ranges include but are not limited to 10 mAU to 100 mAU, 15 mAU to 75 mAU and 25 to 50 mAU.

As described above, the composition that is provided in step a) comprising RNA and a chaotropic agent can be obtained by various means. Suitable, non limiting examples will be described in the following.

According to one embodiment, the composition provided in step a) has been obtained by performing at least the following steps:
obtaining an RNA containing biological sample. Preferably, said sample is a cell containing sample such as in particular a tissue sample or body fluid. Preferably, said sample also comprises DNA. In this case it is also possible to isolate RNA and DNA in parallel from the same sample as will be described in more detail subsequently.
lysing the biological sample wherein the lysis preferably involves the use of at least one chaotropic agent.

Different methods can be used in order to achieve the lysis of the sample and suitable lysis methods are well-known in the prior art. The term "lysis" as used herein refers to the disruption, degradation and/or digestion of a sample or portion or fraction thereof. In a respective lysis step, biomolecules such as in particular nucleic acids can be released from cells or can be freed from other sample additives such as e.g. proteins. Herein, it is referred to a respective step to disrupt, degrade and/or digest a sample generally as lysis step, irrespective of whether biomolecules such as in particular nucleic acids are released from cells or whether the lysis is performed in order to release biomolecules such as nucleic acids e.g. from proteins or other substances comprised in the sample. Hence, the sample may comprise cells or may comprise no or only minor amounts of cells as is e.g. the case with blood plasma. Preferably, for lysis the sample is contacted with one or more lysing agents. RNA should be protected from degradation by nucleases during lysis. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. As discussed above, according to the teachings of the present invention it is preferred that at least one chaotropic agent, preferably at least one chaotropic salt, was used during lysis of the sample. Suitable chaotropic agents and in particular chaotropic salts were described above. Furthermore, during lysis, also other additives can be added such as chelating agents, nuclease inhibitors, in particular RNase inhibitors or DNase inhibitors (in particular if the parallel isolation of RNA and DNA is intended) and the like. Respective additives that can be used to support the lysis of the sample and to protect the released nucleic acids, in particular the released RNA, are well-known in the prior art and thus, do not need to be described in detail herein.

In step d) additional alcohol is added to the mixture to adjust the overall alcohol concentration in the mixture to ≥50% (v/v), preferably ≥55% (v/v), more preferred ≥60% (v/v). By increasing the alcohol concentration to ≥50% (v/v), RNA binding conditions are established that allow to bind small RNA to the nucleic acid binding solid phase. Of course, also longer RNA molecules can bind under these conditions. Suitable ranges for the alcohol concentration in said mixture of step d) include ≥50% (v/v) to ≤80% (v/v), ≥55% (v/v) to ≤75% (v/v) and preferably ≥60% (v/v) to ≤70% (v/v). Suitable alcohols that can be used to establish the RNA binding conditions were described above in conjunction with step b). It is referred to the respective disclosure which also applies here. The same or a different alcohol than was used in step b) can be used in step d). Preferably, the same type of alcohol is used in steps b) and d). Preferably, ethanol or isopropanol is added in step d). By increasing the alcohol concentration in a step-wise manner as described herein and preferably performing a proteolytic digest in step c), RNA binding conditions are provided that are particularly suitable for binding total RNA, including small RNA, with high efficiency even when processing challenging samples such as e.g. fibrous tissue. The step-wise addition of alcohol for establishing the binding conditions as taught herein, wherein an incubation step is performed in between the alcohol addition step, is important to increase the overall RNA yield and in particular to increase the yield of small RNA. As is demonstrated by the examples, said step-wise procedure, in particular when additionally performing a proteolytic digest in step c) has considerable advantages over conventional prior art methods, wherein the alcohol concentration is adjusted for total RNA binding, including small RNA, in a single (or simultaneous) step and wherein accordingly, incubation step c) is missing. The present invention is also favourable over methods, wherein large RNA is bound to a nucleic acid binding solid phase in a first step and small RNA is bound to a further solid phase in a second RNA binding step. When using the method according to the present invention there is no necessity to perform two separate RNA binding steps. Instead, larger RNA and small RNA are bound together to the same nucleic acid binding solid phase. Thus, the same solid phase may be used for binding small RNA and longer RNA. Furthermore, compared to methods that involve an organic extraction with phenol such as phenol/chloroform based methods prior to binding the RNA, the present invention has the advantage that comparable and sometimes even improved RNA isolation results are achieved with the method according to the present invention, wherein, however, the method according to the present invention does not require the use of toxic phenol or other organic extraction steps.

Adding the alcohol in step d) adjusts the binding conditions allowing to bind RNA, including small RNA, to the nucleic acid binding solid phase in step e). In said binding mixture, the chaotropic agent which preferably is a chaotropic salt as described above, is preferably comprised in a concentration which lies in a range of 0.1M up to the saturation limit. Preferred concentration ranges lie, depending on the chaotropic agent used, within 0.3M to 5M, 0.5M to 4M, 0.75M to 3.75M and 1M to 3M. Suitable chaotropic agents and in particular suitable chaotropic salts were described above and include but are not limited to guanidinium hydrochloride, guanidinium thiocyanate, guanidinium isothiocyanate, sodium thiocyanate, sodium iodide, sodium perchlorate, sodium trichloroacetate, sodium trifluoroacetate, urea and the like and in particular preferred are guanidinium hydrochloride, guanidinium thiocyanate and guanidinium isothiocyanate. The chaotropic agent that is present during binding may originate from the lysis procedure or may be added separately to establish the binding conditions. Higher concentrations of chaotropic agents can be favourable to increase the yield of RNA. Thus, it is also within the scope of the present invention to increase the concentration of chaotropic agent for binding, by adding a further amount of chaotropic agent. Furthermore, additional additives can be added to improve RNA binding, e.g. detergents.

In step e) small RNA contained in the mixture resulting from step d) is bound to a nucleic acid binding solid phase as the alcohol concentration is high enough to ensure an efficient capture of small RNA in step e). According to one embodiment, the binding mixture resulting from step d) is contacted with a solid phase for said purpose in step e). This embodiment is particularly suitable if a nucleic acid binding phase comprised in a column is used. If a column based procedure is used, a nucleic acid binding solid phase may be used in step e) in order to bind total RNA, including small RNA, to the solid phase. In this embodiment, preferably no RNA binding to a solid phase occurs prior to step e) and total RNA, including small RNA, is bound for the first time to a solid phase in step e). However, it is also possible to add the nucleic acid binding solid phase prior to step e), e.g. during step a), b), c) or d). E.g. as is shown by the examples, if using particles such as magnetic particles as nucleic acid binding solid phase, the particles can be directly contacted with the composition provided in step a) which is preferred for the ease of handling. Accordingly, the particles can also be present during steps a), b), c) and/or d), and accordingly may be present prior to step e). In this case, RNA, in particular longer RNA molecules, may also bind to the particles prior to step e), e.g. in step c) and or d). In this embodiment, in particular small RNA is bound to the solid phase in step e) because the alcohol concentration is here sufficiently high in the binding mixture (due to the additional amount of alcohol that was added in step d)) to efficiently bind small RNA to the nucleic acid binding solid phase. Irrespective of which of the respective embodiments is used, RNA including small RNA is bound to the solid phase after step e). Suitable nucleic acid binding solid phases will be described in more detail in the following.

As nucleic acid binding solid phase that can be used for binding in step e), any material that is capable of binding RNA can be used. This includes a variety of materials capable of binding nucleic acids under the binding conditions described herein. Exemplary solid phases that can be used in conjunction with the present invention include, but are not limited to, compounds comprising silica, including but not limited to, silica particles, silica fibres, glass fibres, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; minerals, zirconia; alumina; polymeric supports, organic polymers, diethylaminoethyl- and triethylaminoethyl-derivatized supports, hydrophobic chromatography resins and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers and the like. According to one embodiment, the surface of the solid phase such as e.g. the silica solid phase is not modified and is, e.g., not modified with functional groups.

Particularly preferred is the use of silicon containing materials such as silica and polysilicic acid materials, borosilicates, silicates and inorganic glasses as solid phase. Silica based nucleic acid isolation methods are broadly used in the prior art and work particularly well when isolating RNA, including small RNA using chaotropic agents and high alcohol concentrations for binding. The solid phase comprising silica may e.g. have the form of a filter, fibers, membrane or particles. According to the present invention, the use of column based solid phases or the use of particles, in particular magnetic particles, is preferred.

According to one embodiment, accordingly, silica particles are used that may have the form of beads. Preferably, said particles have a size of about 0.02 to 30 µm, more preferred 0.05 to 15 µm and most preferred of 0.1 to 10 µm. To ease the processing of the nucleic acid binding solid phase, preferably magnetic silica particles are used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. The use of magnetic particles is preferred, because the magnetic particles including the bound RNA can be processed easily by the aid of a magnetic field, e.g. by using a permanent magnet. This embodiment is preferred as it is compatible with established robotic systems capable of processing magnetic particles. Here, different robotic systems exist in the prior art that can be used in conjunction with the present invention to process the magnetic particles to which nucleic acids were bound. According to one embodiment, magnetic particles are collected at the bottom or the side of a reaction vessel and the remaining liquid sample is removed from the reaction vessel, leaving behind the collected magnetic particles to which the nucleic acids are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. As respective systems are well-known in the prior art and are also commercially available (e.g. QIASYMPHONY®; QIAGEN), they do not need any detailed description here. In a further alternative system that is known for processing magnetic particles, the sample comprising the magnetic particles can be aspirated into a pipette tip and the magnetic particles can be collected in the pipette tip by applying a magnet e.g. to the side of the pipette tip. The remaining sample can then be released from the pipette tip while the collected magnet particles which carry the bound nucleic acids remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

According to a preferred embodiment, a column based nucleic acid isolation procedure is performed, wherein the solid phase is comprises in a column. Preferably, a nucleic acid binding membrane or nucleic acid binding fibres are used as nucleic acid binding solid phase. Examples include but are not limited to silica membranes, glass fiber membranes, nylon membranes, cellulose membranes such as nitrocellulose membranes, modified cellulose membranes (e.g. acetyl- or hydroxy-), paper membranes, in particular modified papers. Preferably, the membrane is porous. Furthermore, it is preferred to use a membrane or fiber comprising or consisting of silica. Suitable and preferred silica based materials were also described above. A further common nucleic acid binding solid phase comprised in a column is a fill of nucleic acid binding particles, such as silica particles, or a layer of a nucleic acid binding material (e.g. a silica gel). E.g. the silica particles can be arranged as a layer on an inert filter or membrane, thereby forming a nucleic acid binding solid phase. To alleviate the passage of the binding mixture through the nucleic acid binding solid phase comprised in the column, suitable means can be used such as e.g. centrifugation or the use of a pressure difference-generating apparatus which e.g. presses the sample through the column, respectively the nucleic acid binding solid phase or sucks it through the nucleic acid binding solid phase by applying a vacuum. Respective means are well known in the prior art and thus need no further description here. When using a column based approach, it is preferred that the mixture obtained in step d) is contacted with a nucleic acid binding solid phase in step e) in order to bind total RNA, including small RNA, to the nucleic acid binding solid phase. In this embodiment, step e) is the only binding step which aims at binding RNA.

Preferably, the method according to the present invention does not involve the use of phenol, phenol/chloroform and/or chloroform.

After RNA including small RNA was bound in step e) to the nucleic acid binding solid phase, the bound RNA may optionally be washed in step f). For this purpose common washing solutions may be used. According to one embodiment, the solution used for washing comprises at least one chaotropic agent and/or at least one alcohol. Chaotropic agents that can be used in the washing solutions include but are not limited to guanidinium hydrochloride, guanidinium thiocyanate, guanidinium isothiocyanate and sodium iodide. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. However, also washing solutions without a chaotropic agent can be used.

A further suitable washing solution which can be used alternatively or also in addition to the washing solutions described above comprises an alcohol and a buffer. Suitable alcohols and buffers such as biological buffers are described above. Preferably, isopropanol or ethanol, most preferred ethanol is used for this second washing step. Preferably, ethanol is used in a concentration of at least 60% (v/v), at least 70% (v/v), preferably at least 80% (v/v). The buffer is preferably Tris at a pH of approx. 7 to 8. According to one embodiment, the solution used for washing comprises at least one chaotropic agent, at least one alcohol, at least one detergent and/or at least one buffering component.

Either prior to or subsequent to the optional one or more washing steps described above, a DNase digest may be performed while the RNA is bound to the nucleic acid binding solid phase. Thereby, the amount of genomic DNA contaminations in the isolated RNA can be further reduced. Suitable embodiments for performing a respective DNase digest are described herein and are also known in the prior art. A respective DNase digestion step is optional.

The conditions used for performing the DNase digest while the RNA is bound to the nucleic acid binding solid phase can result in that RNA and in particular small RNA is partially released from the nucleic acid binding solid phase. Therefore, it is preferred to ensure that potentially released small RNA is re-bound to the nucleic acid binding solid phase to ensure a high recovery of small RNA. Depending on the type of nucleic acid binding solid phase used, e.g. whether a column based or particle based approach is used, different procedures are feasible.

If particles such as magnetic particles are used as nucleic acid binding solid phase, after performing the optional DNase digest, a chaotropic agent and alcohol can be added, thereby establishing binding conditions that allow to rebind small RNA to the particles. For this purpose, a solution can be used which comprises e.g. a chaotropic salt and/or alcohol. A respective solution may also serve as washing solution. Additional alcohol can also be added separately, in order to increase the alcohol concentration for re-binding. Suitable alcohols, alcohol concentrations, chaotropic salts and chaotropic concentrations were described above in conjunction with step e). The same conditions can be used for rebinding.

If a column based nucleic acid binding solid phase is used it is preferred to perform the following steps after performing the optional DNase digest while the RNA is bound to the solid phase (often also referred to as on-column DNase digest):

collecting small RNA which might have been released from the nucleic acid binding solid phase during the DNAase digest as flow through;

contacting said flow through which comprises small RNA mixed with a recovery solution with the nucleic acid binding solid phase for rebinding the contained small RNA to said nucleic acid binding solid phase.

To ensure that RNA that might have been partially released during the on-column DNase digest rebinds to the nucleic acid binding solid phase and to collect released small RNA as flow through, it is preferred to pass a recovery solution through the column after the DNase digest was completed. RNA that can rebind under the conditions that are established by the recovery solution is tightly rebound to the nucleic acid binding solid phase and "escaped" small RNA can be collected as flow through and thus can be reapplied and accordingly can be rebound to the nucleic acid solid phase that was used in step e). This prevents that small RNA gets lost even if an on-column DNase digest is performed. The recovery solution is accordingly used for collecting potentially "escaped" small RNA and for establishing conditions suitable for re-binding small RNA to the nucleic acid binding solid phase that was used in step e). The recovery solution may also be obtained by mixing one or more solutions and/or ingredients. The binding conditions provided by the recovery solution can be the same or similar to the conditions that are used in step e) for binding RNA including small RNA to the nucleic acid binding solid phase comprised in the column. However, preferably, the recovery solution may also establish binding conditions that are even stronger than the binding conditions used in step e). Preferably, the recovery solution, which may also be obtained by mixing one or more solutions or chemical agents, comprises at least one chaotropic agent and/or at least one alcohol. Suitable chaotropic agents and alcohols were described above. Preferably, the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluroacetate and urea. Preferably, a chaotropic salt is used. In particular, guanidinium hydrochloride and/or guanidinium thiocyanate can be used as chaotropic agent. The concentration of the at least one chaotropic agent in the recovery solution may lie in a range of 0.5M up to the saturation limit. Preferred concentration ranges lie, depending on the chaotropic agent used, in the range of about 1M to 7M, about 1.5M to 6M, about 2M to 5.5M, and preferably lie in the range of about 2.5 to 5.5M.

Furthermore, the recovery solution that is used for binding the collected small target nucleic acids to the nucleic acid binding solid phase may optionally also comprise at least one alcohol. As alcohol, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol, particularly well suitable is isopropanol when isolating RNA as target nucleic acid. It is beneficial to use an alcohol concentration of ≥50% v/v, preferably ≥60% v/v, ≥70%. Preferably, the alcohol concentration lies in a range of about 50% v/v to 90% v/v or about 55% v/v to 85%, more preferred in the range of about 60% v/v to 80% v/v. Details of a respective rebinding step following an on column DNase digest are also described in WO 2012/028737, herein incorporated by reference. After rebinding potentially escaped small RNA to the nucleic acid binding solid phase, again one or more washing steps can be performed. Suitable conditions were described above.

In case it is desired to perform an elution step to elute the RNA from the solid phase, elution can be achieved for example with classical elution solutions such as water, elution buffers, in particular biological buffers such as Tris, MOPS, HEPES, MES, BIS-TRIS Propane and others. Preferably elution solutions are used that do not interfere with the intended downstream application. After elution, the eluate can be heat denatured. However, it is also within the scope of the present invention to release and thus elute the nucleic acids from the solid phase by other elution means such as e.g. heating.

Subsequently, suitable embodiments are described which allow to isolate total RNA including small RNA from a sample comprising RNA and DNA. Here, embodiments are described which allow to selectively isolate total RNA, including small RNA, in parallel with DNA. Thus, RNA as well as DNA can be isolated according to the method of the present invention from the same sample. However, if desired, DNA can also only be selectively eliminated during the purification process thereby providing isolated total RNA, including small RNA, which is free of DNA, in particular genomic DNA. Here, different options exist to remove the DNA. Non-limiting and preferred embodiments will be described subsequently. Furthermore, embodiments are described which are particularly effective in depleting DNA from the sample, thereby increasing the purity of the isolated RNA and avoiding DNA contaminations in the purified RNA.

According to one embodiment, the composition provided in step a) comprises RNA as well as DNA, and RNA and DNA are bound after step e) to the nucleic acid binding solid phase. According to one embodiment, which is feasible if RNA and DNA are both bound to the nucleic acid binding solid phase in step e), a differential elution process can be followed thereby allowing to separately isolate DNA from total RNA, including small RNA. E.g. the DNA can be selectively eluted prior to eluting the bound RNA or vice versa. Respective differential elution conditions are e.g. described in WO 95/21849 or EP 1 693 453.

According to a further embodiment, an intermediate step is included in the RNA isolation process which removes DNA that is comprised in the lysate. According to one embodiment, the DNA is destroyed by adding an appropriate enzyme which specifically destroys DNA such as a DNase. Said enzyme can be added to the lysate or to the composition that is provided in step a). Suitable embodiments for performing a respective DNase digestion step are known in the prior art (see WO 2011/104032) and thus, do not need any further description here.

The lysate obtained from the sample may also optionally be further processed prior to step a). For example, the lysate can be homogenized, which may also occur during the lysis process itself. Furthermore, the lysate can be cleared in order to remove cell debris. Lysate clearing methods may involve filtration and/or binding the cell debris and other contaminants to appropriate surfaces, such as for example surfaces carrying ionic groups, in particular anionic groups such as carboxyl groups.

According to one embodiment, the composition that is provided in step a) has been obtained by performing at least the following steps:
  obtaining an RNA and DNA containing biological sample;
  lysing the sample wherein lysis preferably involves the use of at least one chaotropic salt;
  optionally homogenising the lysate;
  optionally clearing the lysate;
  removing DNA from the lysate.

According to this embodiment, DNA is preferably removed by selectively binding DNA under appropriate conditions to a nucleic acid solid phase and then separating the DNA bound to the nucleic acid binding solid phase from the remaining sample which still comprises the RNA, including small RNA. This can be achieved e.g. by contacting the lysate with a suitable nucleic acid binding solid phase under conditions wherein mainly the DNA but not RNA is bound to the solid phase. Suitable nucleic acid binding solid phases which allow binding of DNA are well-known in the prior art. Furthermore, the nucleic acid binding solid phases described above for the RNA binding step, in particular the silicon containing solid phases, can also be used for DNA binding. Suitable methods for selectively binding and thus removing DNA are for example described in EP 0 880 537 and WO 95/21849, herein incorporated by reference. E.g. if lysing the sample using chaotropic agents such as chaotropic salts in the absence of short chained alcohols such as ethanol or isopropanol, binding conditions can be established that are selective for DNA. If desired, the bound DNA is further used, e.g. further processed and can e.g. optionally be washed and eluted from the nucleic acid binding solid phase thereby providing a DNA fraction which is substantially free of RNA. Thus, the present invention also provides a method wherein RNA and DNA may be isolated from the same sample. However, if the DNA is not of interest, the bound DNA may also be simply discarded if intending to isolate (only) total RNA including small RNA. Also in this case such a DNA binding and removal step is favourable, as it reduces the amount of DNA contaminations in the purified RNA.

When binding DNA to a nucleic acid binding solid phase, such as e.g. a silica containing solid phase, and separating the bound DNA from the remaining sample, a DNA depleted RNA containing composition is provided for step a) of the method according to the present invention.

A preferred embodiment wherein the method according to the present invention is used for isolating DNA and RNA in parallel comprises the following steps:
 obtaining an RNA and DNA containing biological sample;
 lysing the sample wherein lysis involves the use of at least one chaotropic salt;
 optionally homogenising the lysate;
 optionally clearing the lysate;
 wherein the isolation of the DNA comprises the following steps:
  a) removing DNA from the lysate by selectively binding DNA to a nucleic acid binding solid phase and separating the bound DNA from the remaining sample, thereby providing a DNA depleted RNA containing composition which comprises a chaotropic salt and thus provides a composition that can be used in step a) of the RNA isolation;
  b) optionally washing the bound DNA;
  c) optionally performing a proteolytic digest while the DNA is bound to the nucleic acid binding solid phase;
  d) optionally washing the bound DNA;
  e) optionally eluting the bound DNA;
 and wherein the isolation of RNA comprises the following steps:
  a) obtaining the DNA depleted RNA containing composition obtained after step a) of the DNA isolation process, wherein said composition comprises a chaotropic salt;
  b) adding alcohol;
  c) incubating the mixture for at least 2 min, preferably at least 5 min, wherein during said incubation step, preferably a proteolytic digest is performed and wherein preferably for this purpose a proteolytic enzyme is added prior to step b);
  d) adding additional alcohol to the mixture to adjust the overall alcohol concentration in the mixture to ≥50%;
  e) binding RNA contained in the mixture to a nucleic acid binding solid phase;
  f) optionally washing the bound RNA;
  g) optionally eluting RNA from the solid phase.

The individual steps were already explained above and it is referred to the respective disclosure. It is preferred to use nucleic acid binding solid phases which comprise silicon such as a silica or glass nucleic acid binding solid phase for binding the DNA and for binding the RNA. The solid phase may be comprised in a column.

Particular improvements of the DNA isolation step are described in the following. According to one embodiment, a proteolytic digest is performed in step c) of the DNA isolation while the DNA is bound to the nucleic acid binding solid phase. The general advantages of performing a proteolytic digest while the DNA is bound to the solid support and suitable digestion conditions are described in WO2009/016110, herein incorporated by reference. It was found that the on-column proteolytic digest can be substantially improved, if the proteolytic digest occurs in the presence of alcohol and a chaotropic salt. Thus, similar digestion conditions are used as in the proteolytic digest performed in incubation step c) of the RNA isolation procedure. The proteolytic enzyme shows an increased activity in the presence of chaotropic salts and alcohol. For performing the proteolytic digest, a composition comprising alcohol and a chaotropic salt is contacted with the proteolytic enzyme, preferably proteinase K, and the resulting mixture is then contacted with the nucleic acid binding solid phase to which the DNA is bound. Preferably, the resulting mixture which comprises the proteolytic enzyme comprises the alcohol in a concentration that lies in a range selected from 25% (v/v) to 60% (v/v), 30% (v/v) to 55% (v/v), 35% (v/v) to 50% (v/v) and 40%(v/v) to 45% (v/v) and comprises the chaotropic agent which preferably is a chaotropic salt such as a guanidinium salt in a concentration that lies in a range selected from 0.75M to 5M, 1M to 4M, 1.25M to 3.5M and 1.5M to 3.25M, 1.5M to 3M, 1.75M to 2.75M and 2M to 2.5M.

Using these improved digestion conditions involving a chaotropic agent and substantial amounts of alcohol allows to perform the proteolytic digest while the DNA is bound to the solid phase even at lower temperatures such as in a range of 15° C. to 35° C. or 15° C. to 30° C. and accordingly at room temperature. No heating step is required. This is a great advantage as special equipment for heating becomes obsolete, thereby e.g. allowing to integrate the method into automated workflows using robotic systems. Furthermore, the incubation period necessary for a thorough digestion could be reduced by using the novel digestion conditions. E.g. the proteolytic digest achieves substantially the same results irrespective of whether it occurs for 5 min or 30 min. Thus, very short incubation times can be used. These are significant advantages over on-column proteolytic digests known in the prior art.

In order to further reduce the amount of DNA in the isolated RNA, an intermediate step for degrading DNA using a suitable enzyme can be performed after DNA was removed from the lysate by binding the DNA to a nucleic acid solid phase as described above. Performing a DNase digest has the advantage that remaining traces of DNA can be efficiently removed. According to one embodiment, the DNAse digest is performed on the DNA depleted lysate. Suitable conditions are described in WO 2011/104032, herein incorporated by reference. Performing a DNase digest in the lysate prior to RNA binding has the advantage that there is no risk of losing small RNA during the DNase digest. Furthermore, handling steps can be saved compared to an on-column DNase digest. According to a further embodiment, the DNase treatment is performed after the RNA was bound to the nucleic acid binding solid phase. Details were described above. If performing an on-column DNase digest it is preferred to collect potentially escaped small RNA by using a recovery solution as described above. It is referred to the respective disclosure.

The term "sample" is used herein in a broad sense and is intended to include a variety of sources that contain nucleic acids. The sample may be a biological sample but the term also includes other, e.g. artificial samples which comprise nucleic acids. Exemplary samples include, but are not limited to, tissues, including but not limited to, liver, spleen, kidney, lung, intestine, brain, heart, muscle, fat, pancreas, cell cultures, body fluids in general; whole blood; serum; plasma; red blood cells; white blood cells; buffy coat, tumor cells, fetal cells, host and graft cells; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; bone marrow aspirates, cells in suspension, as well as lysates, extracts, or materials obtained from any cells and microorganisms and viruses that may be present on or in a sample and the like. Materials obtained from clinical or forensic settings that contain nucleic acids are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. In particular, the term "sample" refers to a nucleic acid containing sample which also comprises cells. Preferably, the sample is selected from the group consisting of cells, tissue, body fluids such as for example blood, blood products such as buffy coat, plasma and serum, urine, liquor, sputum, stool, CSF and sperm, epithelial swabs, biopsies, bone marrow samples and diverse tissue samples. Exemplary tissue samples were described above. The method according to the present invention is particularly suitable to isolate RNA from fibrous tissue. Fibrous tissues include but are not limited to skeletal muscle, heart and aorta. These fibre-rich tissues are difficult to process due to the abundance of contractile proteins, connective tissue, and collagen. Thus, with many prior art protocols it is not possible to isolate RNA from respective tissues. However, as is shown by the examples, the method according to the present invention allows to efficiently isolate total RNA, including small RNA, from respective samples even though no phenol is used during purification.

The method according to the present invention is also suitable to process blood samples in particular blood samples that were stabilized using for example anticoagulants. Typical anticoagulants that are used for stabilizing blood samples include but are not limited to EDTA and citrate. For isolating RNA, or RNA and DNA in parallel using the method according to the present invention, the blood sample is first treated within an erythrocyte lysis solution to lyse the erythrocytes. Suitable protocols for lysing the red blood cells are known in the prior art. E.g. red blood cells can be selectively lysed by using a red blood cell lysis composition which lysis erythrocytes, i.e. red blood cells, but which does not substantially lyse white blood cells. Any red blood cell lysis buffer known in the prior art can be used for this purpose, respective red blood cell lysis buffers are also commercially available. Suitable examples of standard red blood cell lysis buffers include but are not limited to the erythrocyte lysis buffer ELB1 (320 mM sucrose, 50 mM Tris/Cl pH 7.5, 5 mM $MgCl_2$, 1% TRITON® X-100) or ELB2 (155 mM $NH_4Cl$, 10 mM $KHCO_3$). The white blood cells are then collected for example by centrifugation or by binding the white blood cells to appropriate solid phases suitable for binding white blood cells. The RNA, or RNA and DNA if both types of nucleic acids are of interest, is afterwards isolated from the cell pellet using the method according to the present invention as described above. Here, it is preferred to also include the proteolytic digest during incubation step c) of the RNA isolation protocol as the results are significantly improved. Furthermore, if intending to additionally isolate DNA, it is also preferred to perform a proteolytic digest while the DNA is bound to the nucleic acid solid phase as described above.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. DNA includes, but is not limited to all types of DNA, e.g. gDNA; circular DNA, plasmid DNA and circulating DNA. RNA includes but is not limited to hnRNA; mRNA; extracellular RNA, noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts). Small RNA or the term small RNA species in particular refers to RNA having a chain length of 500 nt or less, 400 nt or less, 300 nt or less, 200 nt or less, 100 nt or less or 50 nt or less and includes but is not limited to miRNA, siRNA, other short interfering nucleic acids, snoRNAs and the like. In case the RNA is a double-stranded molecule, the chain length indicated as "nt" refers to "bp".

This invention is not limited by the exemplary methods and materials disclosed herein. Numeric ranges are inclusive of the numbers defining the range. The headings provided herein are not limitations of the various aspects or embodiments of this invention which can be read by reference to the specification as a whole. The term "solution" as used herein, in particular refers to a liquid composition, preferably an aqueous composition. It may be a homogenous mixture of only one phase but it is also within the scope of the present invention that a solution that is used according to the present invention comprises solid components such as e.g. precipitates. According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

EXAMPLES

Example 1

Isolating RNA Using Magnetic Silica Particles

RNA was isolated from different tissue samples using the method according to the present invention. As tissue samples, 10 mg rat kidney or 20 mg rat muscle was processed per preparation. The protocol according to the present invention was performed as follows:

The tissue sample was lysed and homogenized in a lysis buffer with a concentration of 3,5 M of a guanidinum salt and non-ionic detergents (less than 5%).

The homogenized and lysed sample was then transferred to a robotic system capable of processing magnetic beads (QIASYMPHONY® (QIAGEN)). 20 µl proteinase K and 50 µl magnetic silica beads (MAGATTRACT® G, QIAGEN) was added. The addition steps can be done in any order.

Afterwards, a first amount of ethanol was added thereby providing a mixture comprising ethanol in different concentrations (29% (v/v), 37% (v/v) or 47% (v/v)). The resulting mixture was incubated and mixed for 5 minutes at room temperature. During said incubation step, a proteolytic digest was performed due to the presence of proteinase K.

After said incubation step, additional ethanol is added in a second step to establish a final concentration of 60% (v/v) in the binding mixture. A further mixing step was performed to ensure that the RNA is contacted with and accordingly bound to the magnetic particles.

The bound nucleic acids were washed twice and a DNase digest was performed. For rebinding RNA that were potentially eluted to the particles, a rebinding buffer was added which comprised a chaotropic agent and alcohol and mixed to rebind the RNA. Afterwards, two more washing steps were performed with alcohol containing wash buffers. The magnetic particles with the bound RNA were air dried to evaporate the alcohol and the RNA was eluted with RNase free water.

For comparison, the following protocols were performed:

In the first protocol, the same procedure was followed, wherein, however, the final concentration of ethanol was 37% (added in one step). This corresponds to a standard RNA isolation procedure which does not aim at specifically capturing small RNAs such as miRNA in the isolated total RNA.

In the second protocol, the concentration of ethanol was adjusted in the first step to 60% (and thus the final ethanol concentration that is needed for efficient binding of the small RNA). Thus, in this variant no stepwise approach as is taught by the present invention is followed.

Figure 2:
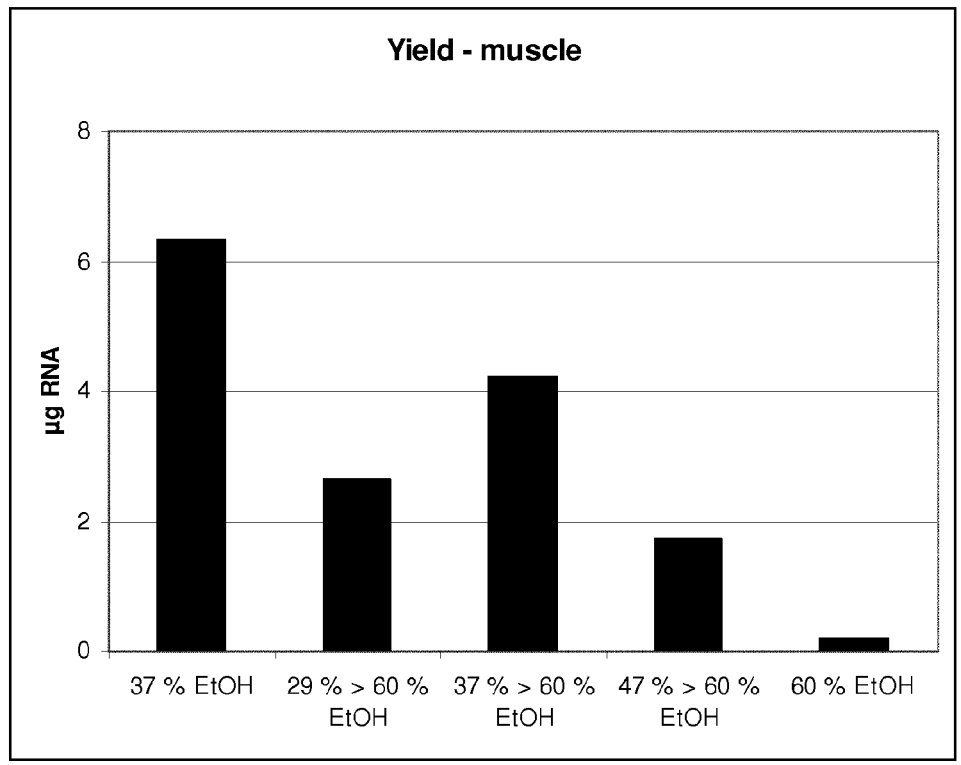
FIG. 2: Shows the RNA yield obtained with muscle tissue following either prior art approaches or the step-wise addition of alcohol according to the principle of the invention (see example 1).

The results are shown in FIGS. 1 and 2. FIG. 1 shows the results that were obtained with the kidney tissue samples. With the standard RNA isolation protocol which uses 37% ethanol in the binding mixture, approximately 12 µg RNA was recovered. Adjusting the ethanol concentration to 60% in one step resulted in dramatically reduced RNA yields. If the alcohol concentration was adjusted in one step to 60% ethanol in order to allow the capture of small RNA, only approximately 3.5 µg RNA was recovered. In contrast, following the stepwise approach as is taught by the present invention resulted in similar or even higher yields as compared to the standard protocol which uses 37% ethanol. Particularly improved results with respect to the RNA yield were achieved if in a first step the alcohol concentration was adjusted to 37% and then in the second step to 60% ethanol. Here, the overall RNA yield was even significantly improved compared to the standard protocol, as approximately 16 µg RNA could be recovered. FIG. 1 thus demonstrates the particular advantages that are achieved with the method according to the present invention. It allows to isolate total RNA with good yields and furthermore also allows to capture small RNAs, such as miRNAs, which cannot be captured using a standard protocol that uses only 37% ethanol. The recovery of small RNA was also confirmed by testing (detection of RNA miR-16 using the miScript system). The difference between the standard protocol (37%, one step) and all other protocols which due to the higher alcohol concentration in the binding mixture also allow to isolate small RNA was between 3.5 and 5 PCR cycles, which corresponds to a more than ten times lower miRNA recovery at the lower ethanol concentration (data not shown) compared to the protocols which use 60% in the binding mixture. This confirms that high alcohol concentrations of more than 50%, preferably of approximately 60% (v/v) are required to efficiently capture small RNAs. However, if the alcohol concentration is adjusted to 60% in one step, the overall yield of RNA is dramatically reduced. Following the teachings of the present invention and adding the alcohol in a stepwise manner allows to overcome this drawback and accordingly allows to isolate total RNA with good yield, which additionally includes the small RNAs.

FIG. 2 shows the results for the muscle samples. Again, it is demonstrated that a stepwise alcohol addition as is taught by the present invention provides higher yields of total RNA compared to a protocol, wherein the alcohol concentration is adjusted in one step to 60%.

Example 2

RNA Isolation Using a Column Based Approach

RNA including small RNAs was purified from 10 mg of RNALater stabilized rat muscle tissue using the method according to the present invention. The isolation procedure was as follows:

Preparation of the Lysate 10 mg tissue is homogenized in 350 µl of a chaotropic agent containing buffer (RLTplus, QIAGEN plus beta-mercaptoethanol) using a rotor stator, polytron or bead mill.

Removal of DNA

350 µl of the lysates were applied to Allprep-DNA-spin columns and centrifuged for 1 minute at 14.000 rpm. Thereby, genomic DNA (but not the RNA) is bound to the spin column and the flow-through can be used for RNA preparation. If desired, the bound DNA can also be further processed in order to provide the DNA as separate fraction. Thus, this protocol also allows the parallel isolation of DNA and RNA from one sample. In this experiment, the DNA was not further processed, but discarded.

Isolation of RNA

The RNA is isolated from the DNA depleted flow-through that is obtained after the DNA was removed from the lysate. The DNA-depleted RNA containing flow-through was mixed with 50 µl proteinase K. To said mixture, ethanol was added up to a final concentration of 36% in the mixture. In a variation, isopropanol was added. For comparison, no ethanol was added to the mixture. Samples were then incubated at room temperature for 15 minutes in order to perform the proteolytic digest after which more alcohol (ethanol or isopropanol) was added to adjust the RNA-binding conditions to a final alcohol concentration of 63% (v/v) or 60% (v/v). The resulting mixture was applied to an RNeasy-mini-column and centrifuged for 1 minute at 14.000 rpm. The flow-through was discarded.

Afterwards, the column-bound RNA was washed and the RNA was eluted. No on-column DNase digest was performed.

As control and for comparison, the miRNeasy protocol was performed. The miRNeasy protocol is a phenol/chloroform-based method which allows the isolation of high amounts of pure RNA, including small RNA. One aim of the present invention was to provide a phenol/chloroform-free method which is capable of producing similar results.

Figure 4:
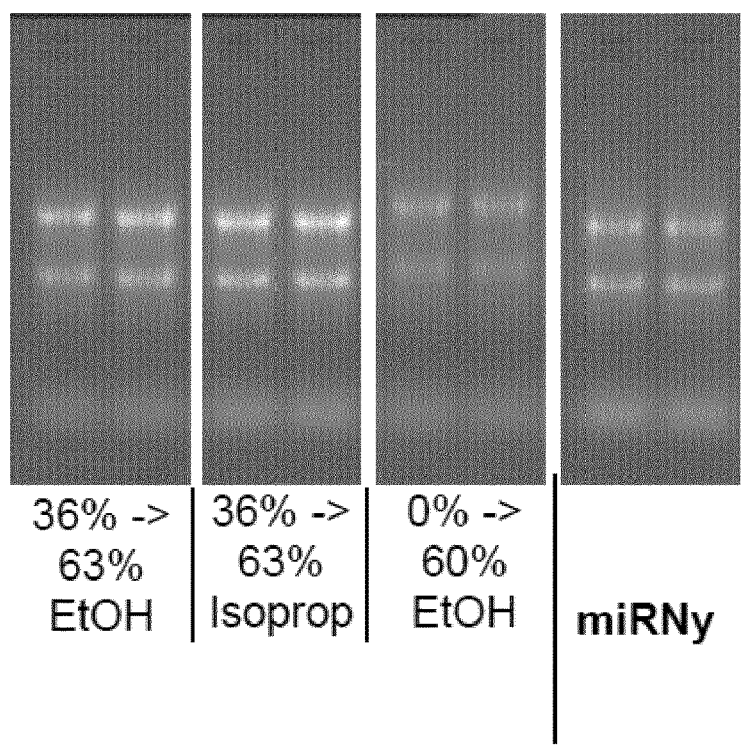
Figure 5:
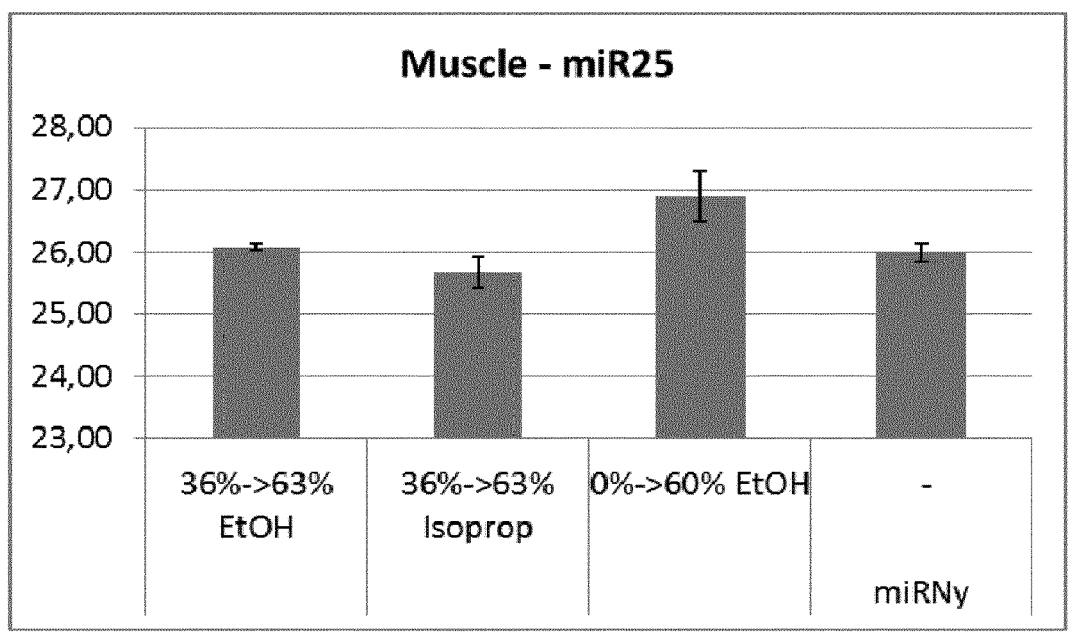
FIG. 5: miRNA assay results according to example 2.

The RNA yield was determined by Nanodrop measurement. The same volume of eluates was used as template in the miScript miRNA assay miR-25 and for gel electrophoretic analysis. The results are shown in FIGS. 3-5.

Figure 3:
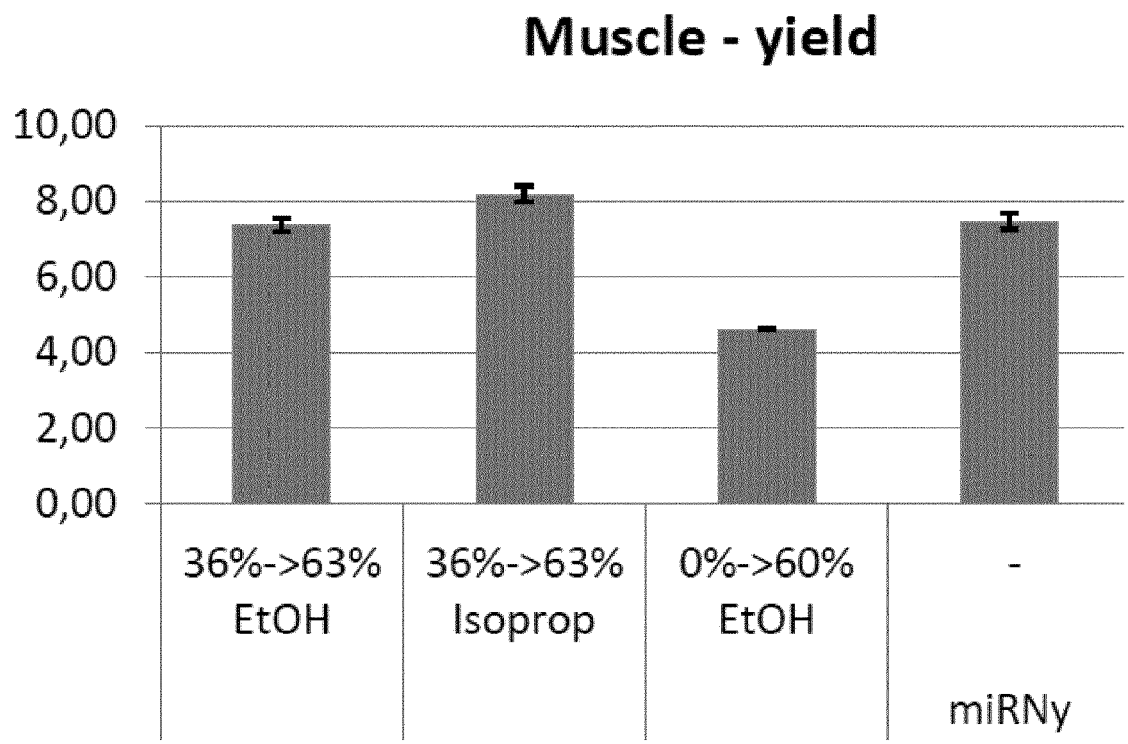
FIGS. 3 and 4: Show the RNA yield obtained with muscle tissue following either prior art approaches or a step-wise addition of alcohol according to the principle of the invention (see example 2) as diagram (FIG. 3) and picture obtained after gel electrophoresis of the isolated RNA (FIG. 4).

FIG. 3 shows the overall RNA yield that was obtained by using the different methods. As can be seen, the protocol according to the present invention, wherein the alcohol is added in a stepwise approach provided similar yields as the miRNeasy control. The same results are obtained for ethanol and isopropanol confirming that different alcohols can be used for that purpose.

However, if no stepwise approach was followed but instead the ethanol was added directly in one step to adjust the alcohol concentration in the binding mixture to 60%, significantly lower yields were obtained. The results are also confirmed by the gel pictures after electrophoresis (see FIG. 4). In addition, also the results of the miRNA assay (see FIG. 5) confirm the improvements that are achieved with the method according to the present invention. RNA isolated by the method according to the present invention, wherein the alcohol is added in a stepwise manner, achieves Ct values in the RT-PCR analysis, which are comparable to RNA that is isolated with the phenol/chloroform-based miRNeasy kit control. This confirms the high performance of the method according to the present invention. Furthermore, FIG. 5 shows that if a respective stepwise approach is not followed but instead the alcohol is directly added in one step, this also results in significantly lower miRNA recovery as can be derived from the higher Ct values.

On balance, this example shows that the overall yield could be improved due to the stepwise addition of alcohol by approximately 1.5 fold and also the miRNA recovery could be significantly improved. This finding was confirmed in repeated experiments using either ethanol or isopropanol for adjusting the RNA binding conditions.

Example 3

Isolation of RNA from Different Tissues Using a Column-based Approach

The method according to the present invention (see example 2) was compared to different protocols, processing brain, heart and liver samples.

RNA from heart, brain and liver tissues was isolated using the method according to the present invention with a proteinase K digestion of the RNA containing flow-through and a stepwise alcohol addition (see example 2) or different variations. The lysis buffer was used with concentrations of 3.5 M GTC and 3 M GTC for purification. The following variations were tested:

Variation (A) (invention): 50 µl proteinase K is added prior to dilution with 0.66 volumes of ethanol. The indicated volume of ethanol refers to the volume of the lysate/flow-through that is present prior to adding the proteinase K.

Variation (B): 50 µl proteinase K is added prior to dilution with 0.166 volumes of $H_2O$. The indicated volume of ethanol refers to the volume of the lysate/flow-through that is present prior to adding the proteinase K.

Variation (C): 50 µl proteinase K is added to the RNA containing flow-through but remains undiluted for the proteinase K digestion.

The samples were incubated for 15 minutes at room temperature gently shaking, thereby digesting the sample (Proteinase K digest). For the subsequent RNA column binding, 100% ethanol was added up to final concentration of 60% in the binding mixture to allow the co-purification of small RNAs.

Figure 6:
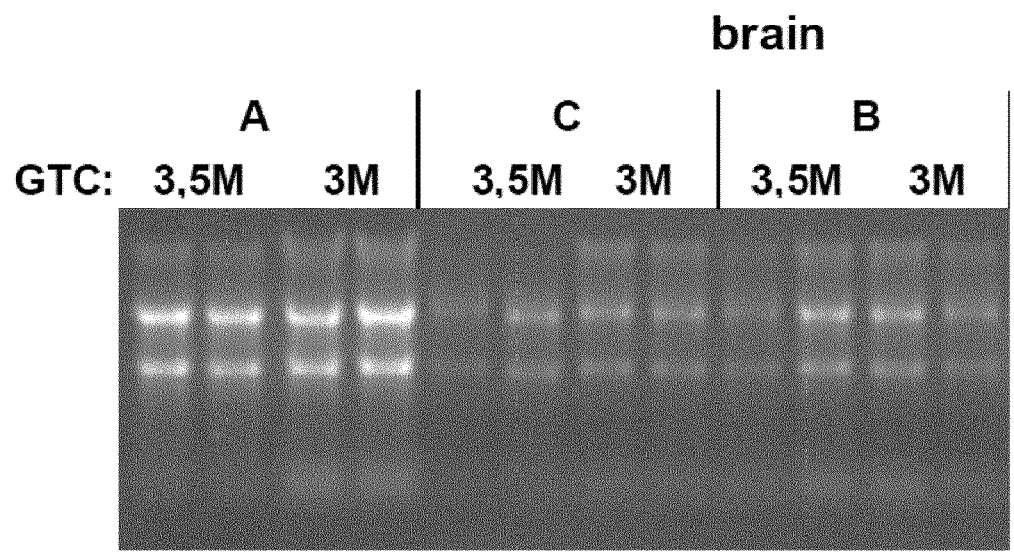
FIGS. 6 to 8: Show the RNA isolation results obtained with different tissues (FIG. 6—brain.
Figure 7:
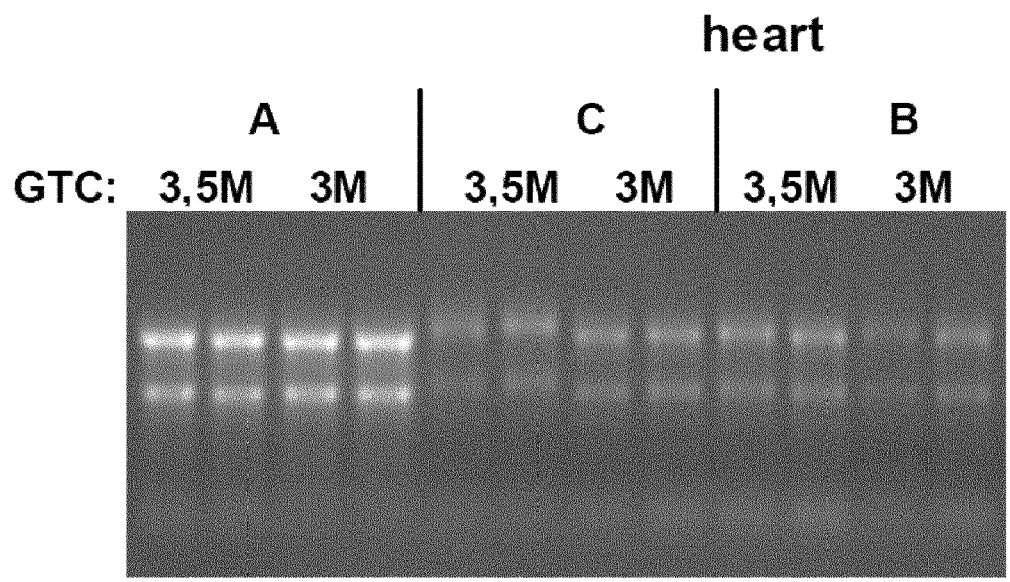
Figure 8:
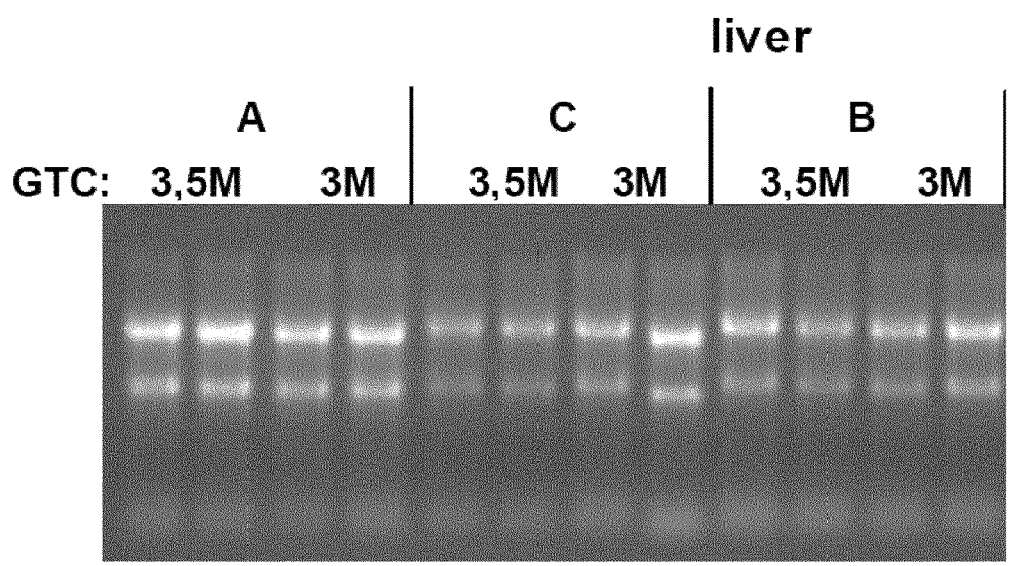

The same volumes of eluates were analyzed on an agarose gel. The results are shown in FIGS. 6, 7 and 8, respectively. As can be seen, the method according to the present invention (A) provides significantly higher yields than methods wherein no stepwise addition of alcohol is performed. Furthermore, the comparison with a dilution of the lysate with water (B) also demonstrates that the beneficial effect that is seen with the method according to the present invention is caused by the stepwise addition of alcohol and is not attributable to a simple lysate dilution effect. The considerable improvements that are obtainable when following the teachings of the present invention regarding the obtainable RNA yields is again confirmed. The eluates were also analyzed as template in a quantitative, real-time RT-PCR assay for miRNAs (miR-25) and for the larger mRNAs (madh-7 gene). The results confirm (see results with madh-7) that the method according to the present invention results in higher overall RNA yields. The yields of miRNA were comparable. Similar results were also obtained in other tissue samples, such as fat, muscle and lung. Here, the miRNA yields were also comparable to the results that are achieved with the phenol/chloroform-based miRNeasy method (data not shown).The comparison of the tested chaotropic agent concentrations (3.5 M GTC and 3 M GTC) in the lysis buffer showed no differences in the performance of the tested tissue types. FIGS. 6-8 demonstrate the obtainable yield differences in brain, liver and heart tissue and thus demonstrate the advantages when performing the proteinase K digestion in a chaotropic salt (GTC)/ethanol mixture compared to procedures wherein the lysate is not diluted or diluted by the addition of $H_2O$. It is an advantage if no dilution with $H_2O$ is performed, because a dilution with $H_2O$ severely increases the amount of liquid which needs to be processed subsequently, and accordingly increases the amount of alcohol that must be added in order to achieve an alcohol concentration of more than 50%, preferably at least 60% in the RNA binding mixture. Handling such large sample volumes is inconvenient for the user, as the binding mixture must potentially be applied more than once to the spin column in order to ensure that the whole binding mixture has passed through the column. Also, in this respect the method according to the present invention provides a significant advantage, as the overall amount of sample volume is kept low.

It is preferred to use a concentration of 3.5 GTC in the lysis buffer, as it improves the DNA performance and thus the DNA removal. As can be seen in FIGS. 6-8, no genomic DNA contaminations were observed in samples obtained from heart tissue. DNA contaminations were also not found in RNA isolated from fat, muscle or lung. However, minor amounts of DNA were identified in RNA isolated from brain and less distinctively also when isolating RNA from liver tissue. For respective tissues it is therefore preferred, to perform an additional on-column DNase digestion as described herein. Thereby, DNA-free RNA eluates are provided using the methods of the invention also from those tissues.

Example 4

Improvement of the DNA Isolation Step

As described herein, the method according to the present invention can be used to isolate RNA and DNA in parallel from the same sample. The general approach for isolating DNA is known in the prior art and is correspondingly performed herein. Regarding the lysis of the sample and the binding of the DNA to the spin column, we refer to the description of example 2. After the DNA was bound to the spin column, the DNA depleted flow-through can be used for the RNA preparation. The bound DNA can then be washed using a suitable wash buffer, comprising for example a chaotropic salt and alcohol and the column is centrifuged for 1 minute at 14.000 rpm. The flow-through is discarded.

To improve the DNA isolation, a proteolytic digest is performed, while the DNA is bound to the solid phase. A respective on-column proteolytic digest is known in the prior art (see for example WO 2009/016110). Example 4 shows that the DNA yield could be significantly improved, if the proteolytic digest is performed in a solution comprising a chaotropic agent and alcohol. It was even possible to perform the proteolytic digest at room temperature so that it was not necessary to maintain an elevated temperature of for example 56° C. during the proteolytic digest. The specific embodiment according to the present invention, wherein the on-column proteolytic digest is performed in a chaotropic/alcohol milieu even showed improved results over standard methods, wherein the digestion is performed in water at 56° C.

These advantageous results were demonstrated by the following experiments:

The DNA was purified using the method according to the present invention (see example 2). An on-column proteinase K digestion was performed while the DNA was bound to the column (UAP). The on-column proteinase K digestion was performed either in water at 56° C. (A) or in a chaotrope-ethanol milieu at room temperature (B). For establishing the chaotrope-ethanol milieu, 20 μl proteinase K was mixed with a solution, comprising 3M GTC and approximately 60% ethanol.

As a control, a traditional protocol (Allprep DNA/RNA) was performed, which is basically the same regarding the DNA binding step, but wherein no proteinase K digestion is performed on the column (AP old).

Figure 9:
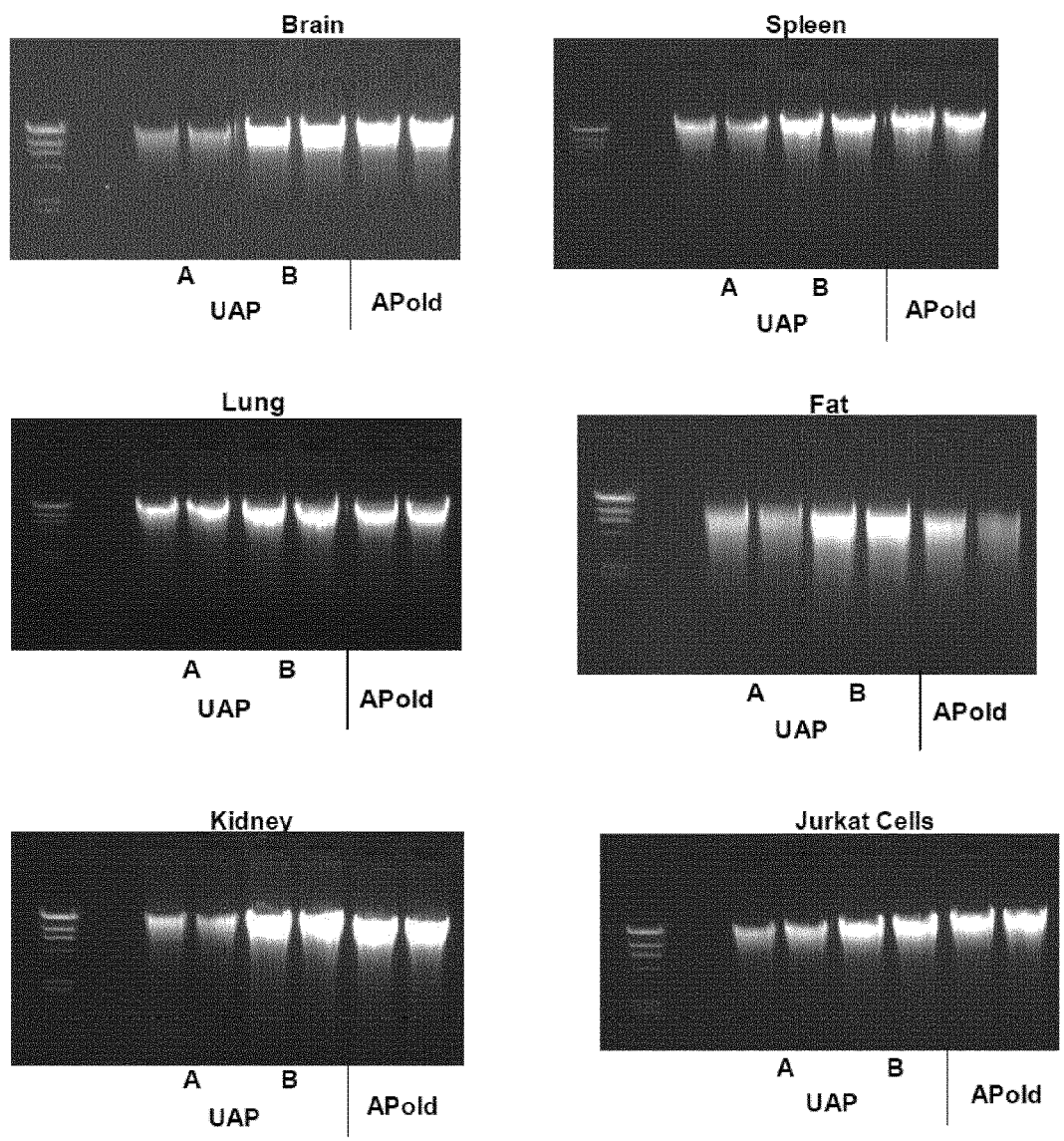
FIG. 9: Shows the RNA isolation results obtained with different tissues following different isolation protocols (see example 4). Shown are pictures obtained after gel electrophoresis of an aliquot of the isolated RNA.

The results are shown in FIG. 9 for different tissue types. Therein, gel electrophoresis was done with the same volume of eluates.

As can be seen from the results, introducing a proteinase K digestion while the DNA is bound to the nucleic acid binding solid phase, results in that the DNA yields can be improved for certain tissue types such as for example lung, fat and kidney if the digest is performed in a chaotropic agent/alcohol milieu as taught herein.

Furthermore, it was tested whether the incubation during the proteolytic digest while the DNA is bound to the nucleic acid binding solid phase can be securely performed at different "room temperatures" that might occur in different laboratories. Therefore, temperatures from 15 to 25° C. and 30° C. were tested. The DNA was purified from various RNALater stabilized rat tissues using the protocol according to the present invention with an on-column proteinase K digestion during the DNA preparation step at different temperatures as indicated (+PK). As control, the traditional Allprep protocol (APold) without on-column proteinase K digestion was performed. The DNA yield was determined by Nanodrop measurement.

Figure 10:
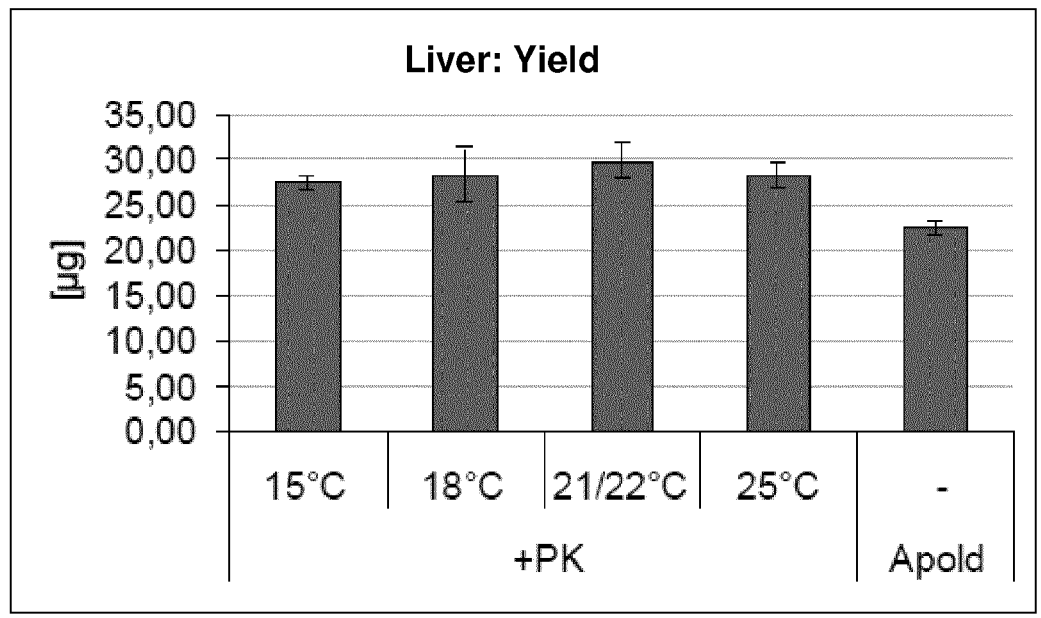
FIG. 10: Influence of the temperature on the on-column proteolytic digest performed during the DNA isolation step and on the DNA yield (see example 4).
Figure 10:
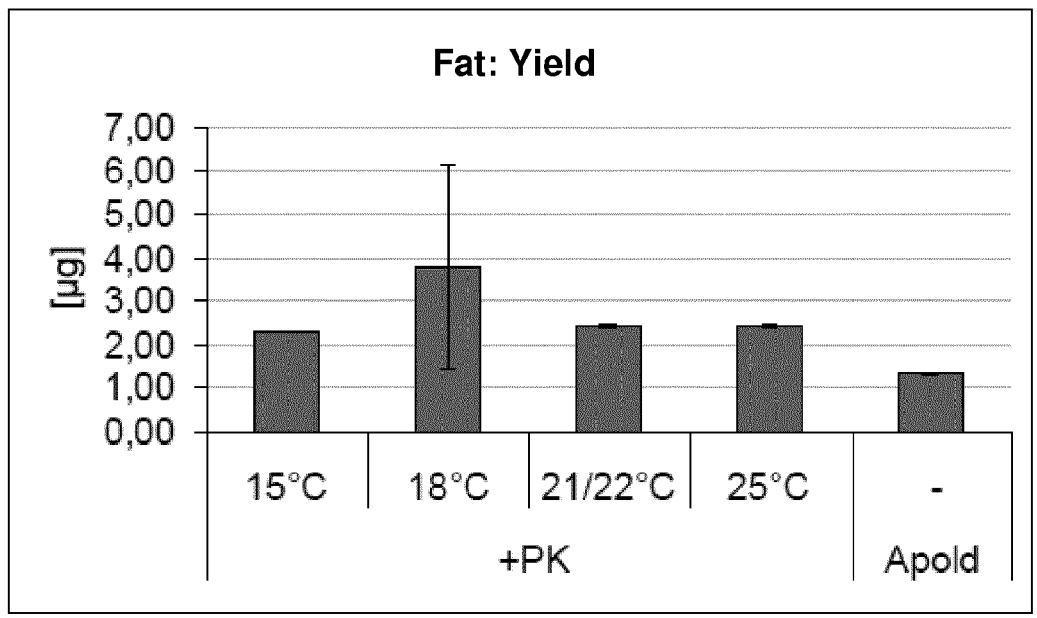
Figure 10:
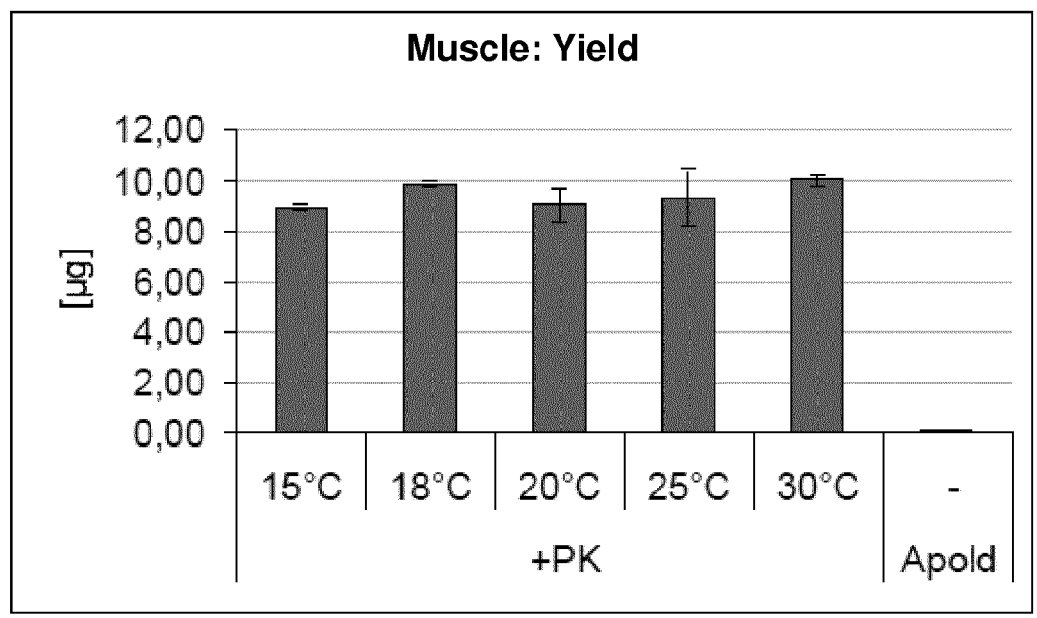

The results are shown in FIGS. 10 *a*) to *c*). All temperatures tested showed comparable yields, indicating that the proteolytic digest has worked properly. Furthermore, these examples show that the yield of DNA can be particularly low from certain tissues such as muscle, if no additional proteolytic digest is performed while the DNA is bound to the nucleic acid binding solid phase. Therefore, performing the on-column proteolytic digest in a chaotrop/alcohol mixture as taught herein, has significant advantages.

Figure 11:
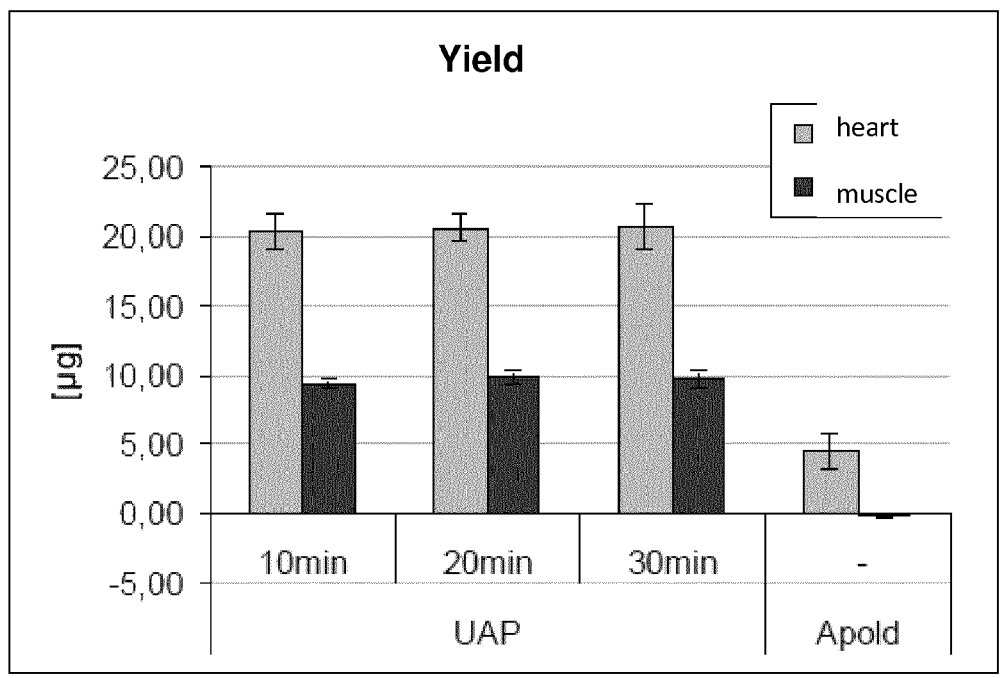
FIG. 11: Influence of the incubation time on the on-column proteolytic digest performed during the DNA isolation step and on the DNA yield (see example 4).
Figure 11:
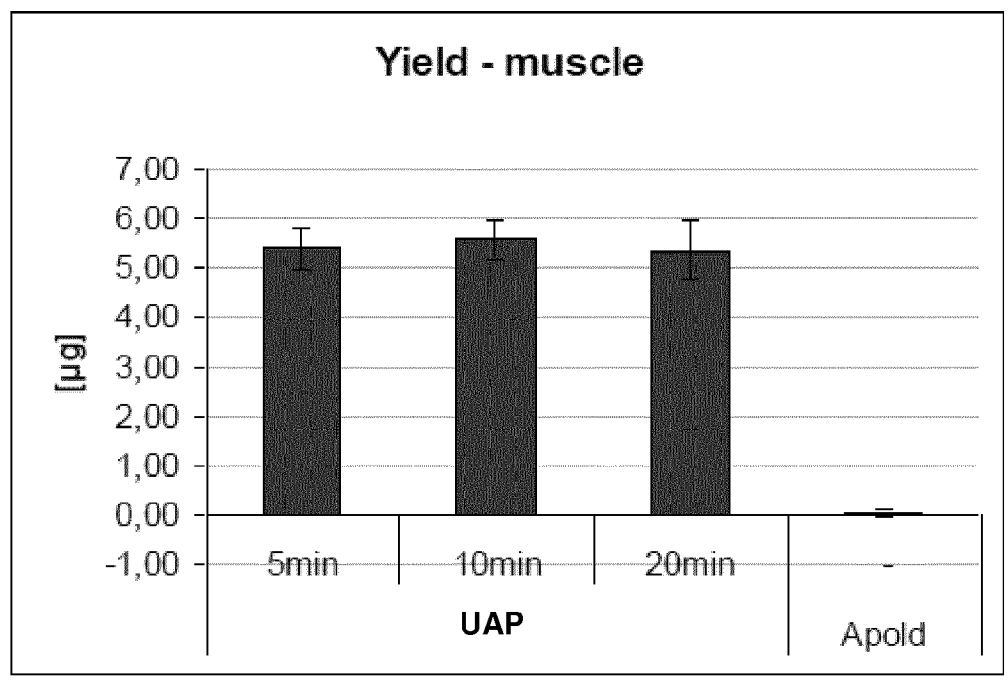

Furthermore, in order to save time it was analyzed whether the incubation times necessary for the proteolytic digest while the DNA is bound to the nucleic acid binding solid phase can be reduced. DNA was purified from RNALater stabilized rat heart and muscle tissue using the new protocol according to the method of the present invention, including in the DNA binding step an on-column proteinase K digestion for 5, 10, 20 and 30 minutes. As control, the traditional Allprep protocol (AP old) without on-column proteinase K digestion was performed. The DNA yield was determined by Nanodrop measurement. The results are shown in FIGS. 11*a* and 11*b*. Incubation periods from 5 to 30 minutes showed comparable yields far higher than yields obtained with the old protocol, which did not include a proteolytic digest while the DNA is bound to the nucleic acid binding solid phase. Consequently, it is possible to used very short incubation times such as for example 5 minutes or even less.

Example 5

RNA Isolation Using a Stepwise Addition of Ethanol and Proteinase K Digestion

RNA including small RNAs from 10 mg of RNALater stabilized rat muscle tissue was isolated using the method according to the present invention, wherein a proteinase K digestion is performed on the Allprep mini spin flow-through from which the DNA was depleted by selectively binding the DNA to a suitable nucleic acid binding solid phase (see example 2 for details). First, 50 μl proteinase K was added to the lysate and then either (A) the full volume of ethanol needed for generating RNA binding conditions of 60% or (B) only half of it with setting concentration to 46% was pipetted to the mixture followed by a 15 minutes incubation step at 21° C. for proteinase K digestion. To the latter (B) the second half of ethanol necessary to reach a final concentration of 60% for RNA column binding was added after the proteinase K digestion was performed. Accordingly, setting B corresponds to the method of the present invention, wherein the alcohol needed to establish the binding conditions is added stepwise.

Figure 12:
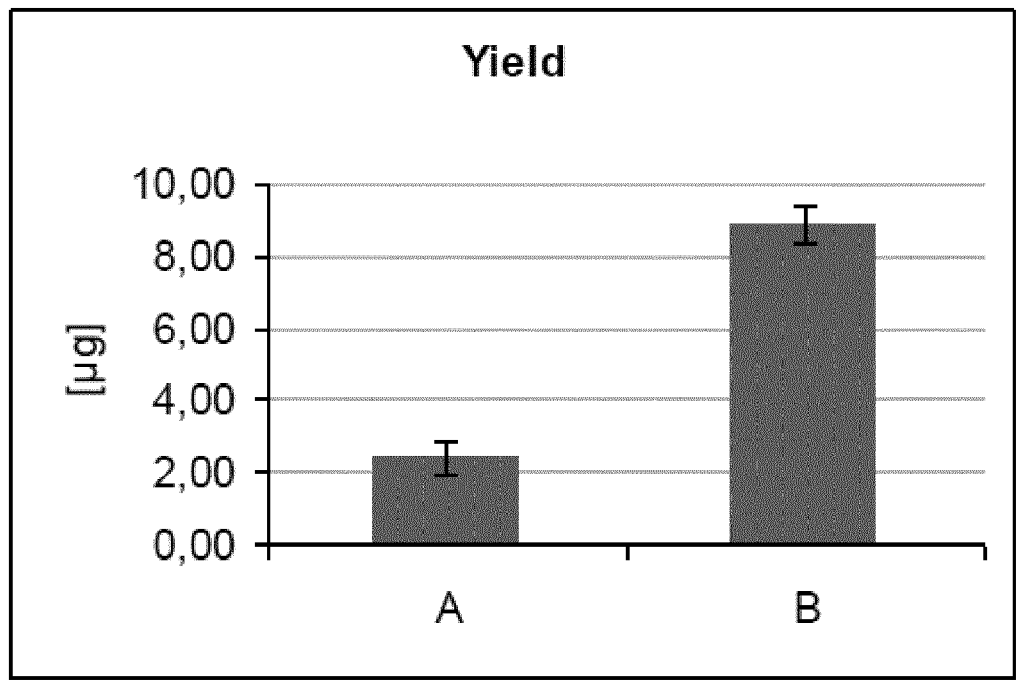
FIGS. 12 to 14: Shows the RNA isolation results obtained from muscle tissue following different isolation protocols (see example 5). Shown are diagrams of the overall yield (FIG. 12) and miRNA assay results (FIG. 14) and a picture obtained after gel electrophoresis of an aliquot of the isolated RNA (FIG. 13).
Figure 13:
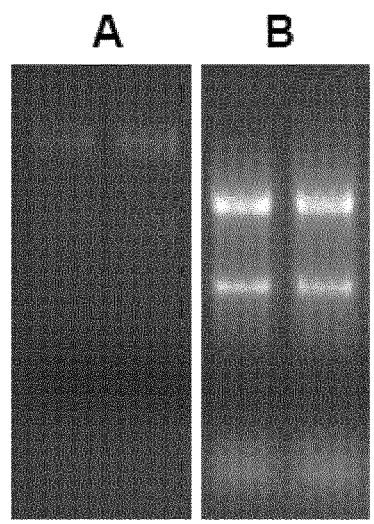
Figure 14:
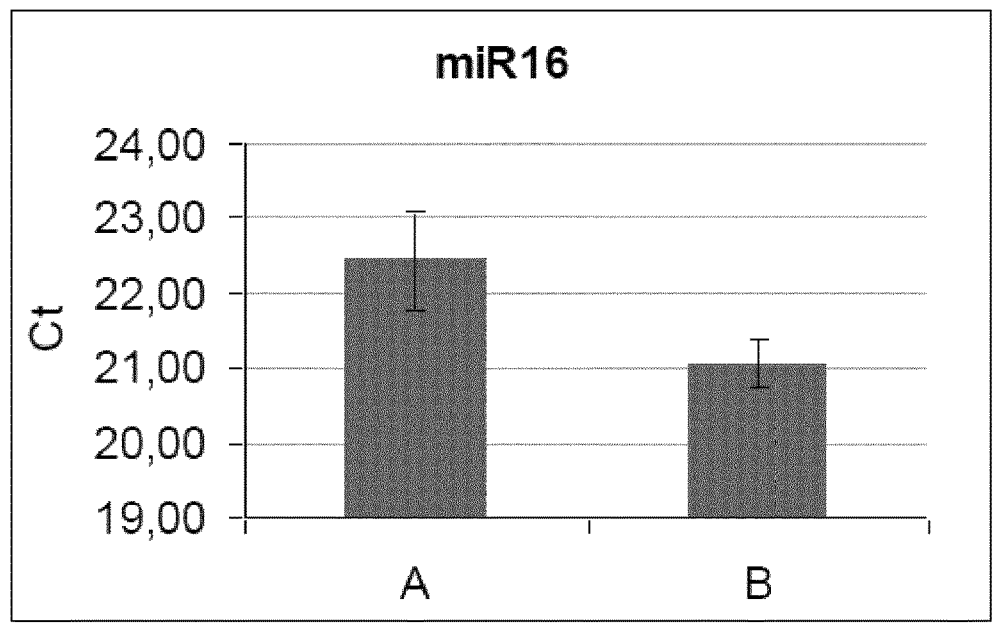

The overall RNA yield was determined by Nanodrop measurement. The same volume of eluate was used as template in a miRNA Assay miR-16. Gel electrophoresis was done with the same volume of eluates. The results are shown in FIGS. 12, 13 and 14, which again confirm the advantages achieved with the method according to the present invention.

Figure 15:
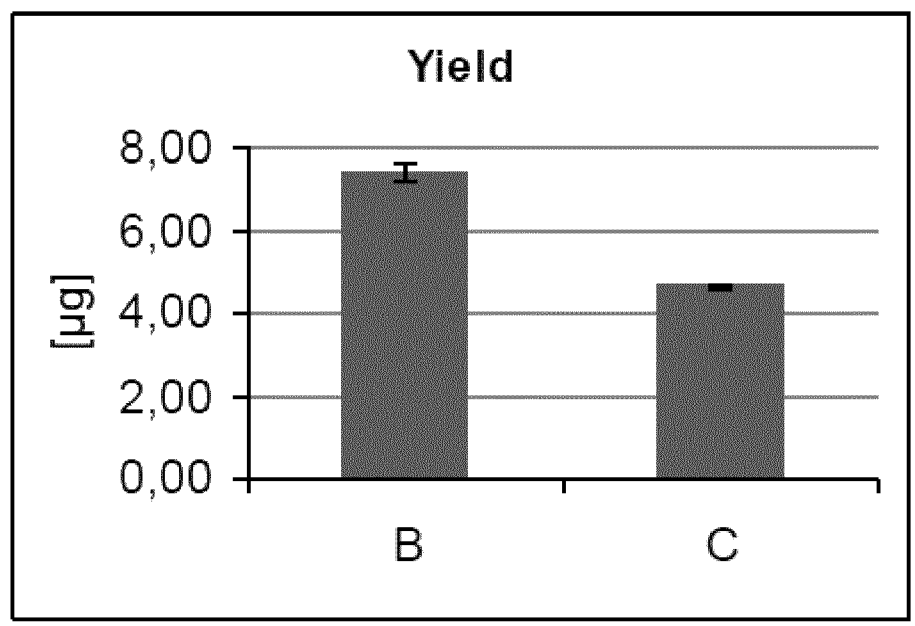
FIGS. 15 to 17: Shows the RNA isolation results obtained from muscle tissue following different isolation protocols (see example 5). Shown are diagrams of the overall yield (FIG. 15) and miRNA assay results (FIG. 17) and a picture obtained after gel electrophoresis of an aliquot of the isolated RNA (FIG. 16).
Figure 16:
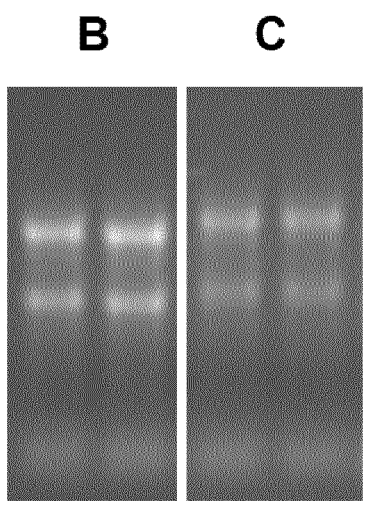
Figure 17:
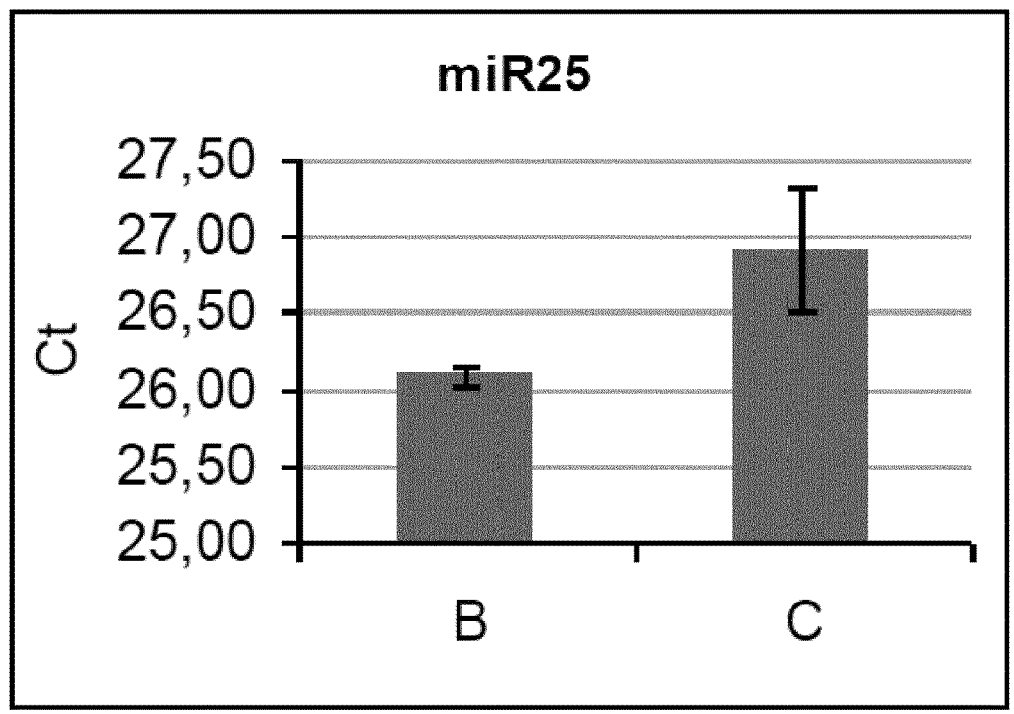

Furthermore, RNA including small RNA was purified from 10 mg of RNALater stabilized rat muscle tissue using the method according to the present invention with proteinase K digestion of the DNA depleted Allprep mini spin column flow-through. After addition of 50 μl proteinase K either an aliquot of ethanol with a final concentration of 36% (B) or no ethanol (C) was added to the mixture for the subsequent incubation at room temperature for 15 minutes for proteinase K digestion. Afterwards, the volume of ethanol necessary for binding to the RNeasy spin column was adjusted to a final concentration of 60% in all samples. Variant B accordingly corresponds again to the method according to the present invention. The RNA yield was determined again by Nanodrop measurement. The same volume of eluate was used as template in miRNA Assay miR-25. Additionally, gel electrophoresis was done with the same volume of eluates. The results are shown in FIGS. 15, 16 and 17 and again confirm the advantages of following a stepwise alcohol addition.

Furthermore, it was analyzed which incubation times provides best results for the proteolytic digest. Here, RNA including miRNA war purified from RNALater stabilized rat fat and muscle tissue using the protocol according to the present invention, with a proteinase K digestion after the addition of the first ethanol volume (adjusting the concentration in the mixture to 37% (v/v)) for 5, 10, 15 or 30 minutes. The obtained yield was determined by Nanodrop measurement. The same volume of eluate was used as template for RT-PCR analysis in a miRNA Assay miR-25 and the longer mRNA amplicon madh-7.

As a control, RNA purification was carried out using the miRNeasy kit.

In a preferred embodiment, when processing tissue containing a high fat content like adipose and brain it is preferred to perform an additional chloroform extraction step. For this purpose, the flow-through that is obtained after DNA depletion is mixed with chloroform and shaken vigorously for 10 to 15 seconds. Afterwards, the mixture is centrifuged at full speed for 3 minutes at 4° C. The supernatant (aqueous phase) is then transferred to a new vessel and thereby provides a composition comprising RNA and a chaotropic salt for step A of the RNA isolation method according to the present invention. The RNA is then isolated from the respective aqueous phase using the protocols described herein. Thus, as a next step, proteinase K is added.

Figure 18:
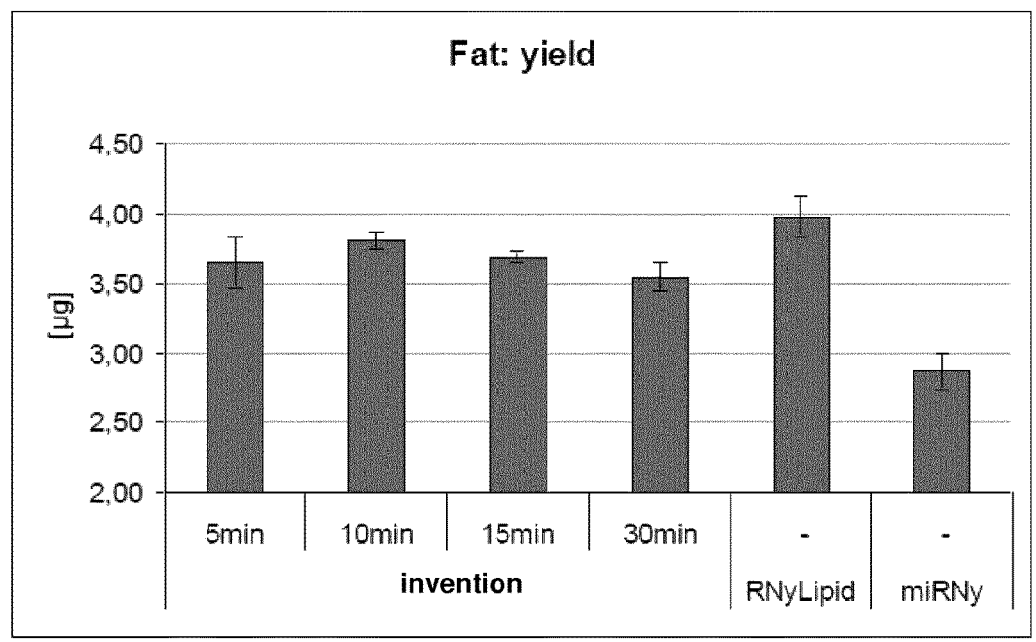
FIGS. 18 and 19: Shows the RNA isolation results obtained from muscle tissue following different isolation protocols (see example 5). Shown are diagrams of the overall yield (FIG. 15) and miRNA assay results (FIG. 17) and a picture obtained after gel electrophoresis of an aliquot of the isolated RNA (FIG. 16).
Figure 18:
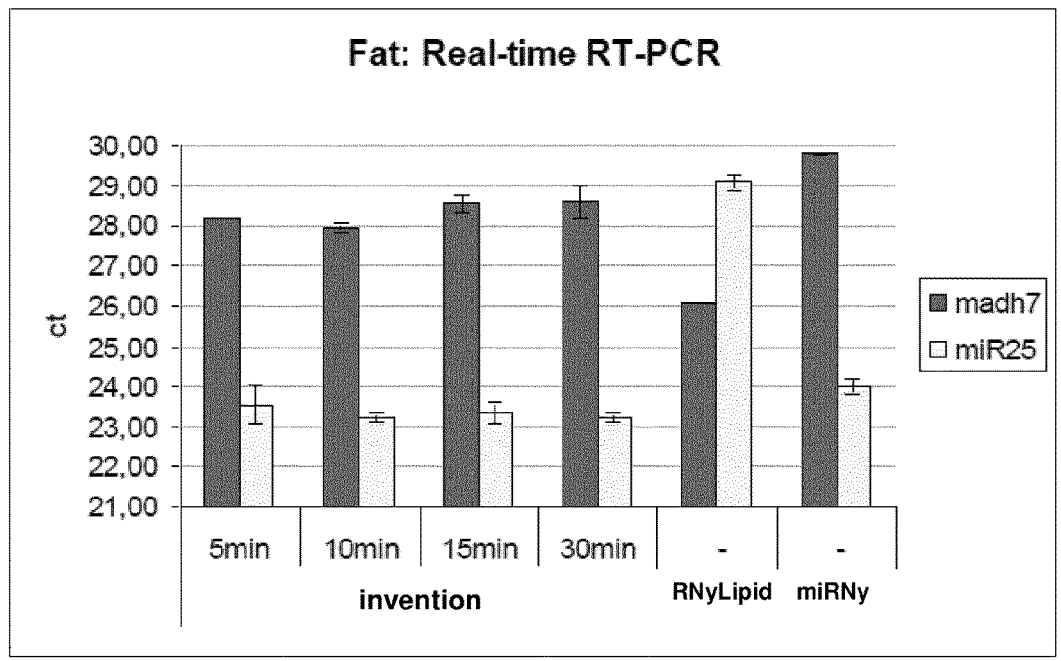
Figure 19:
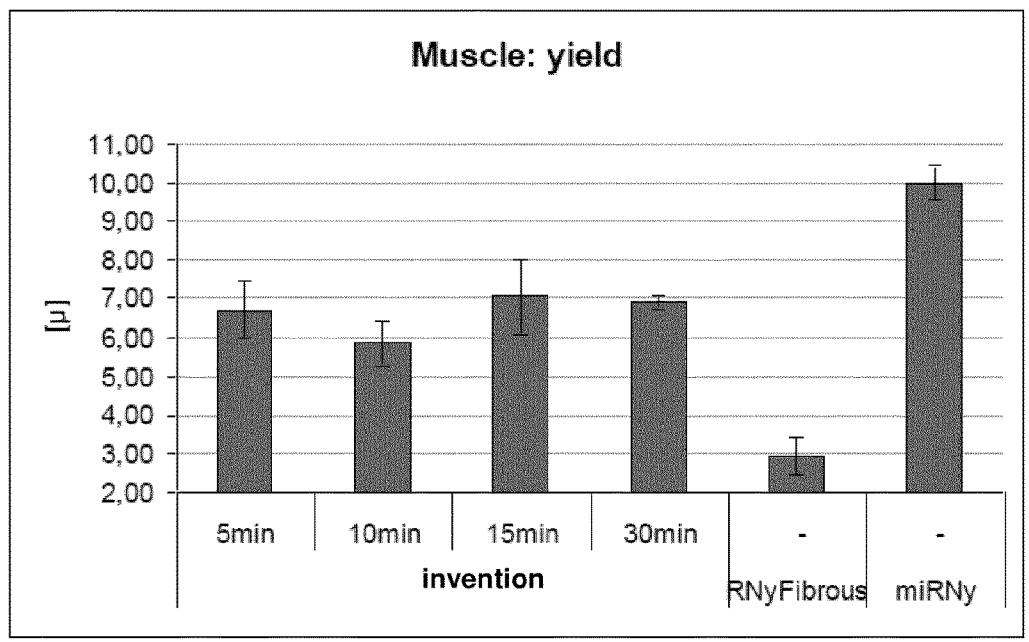
Figure 19:
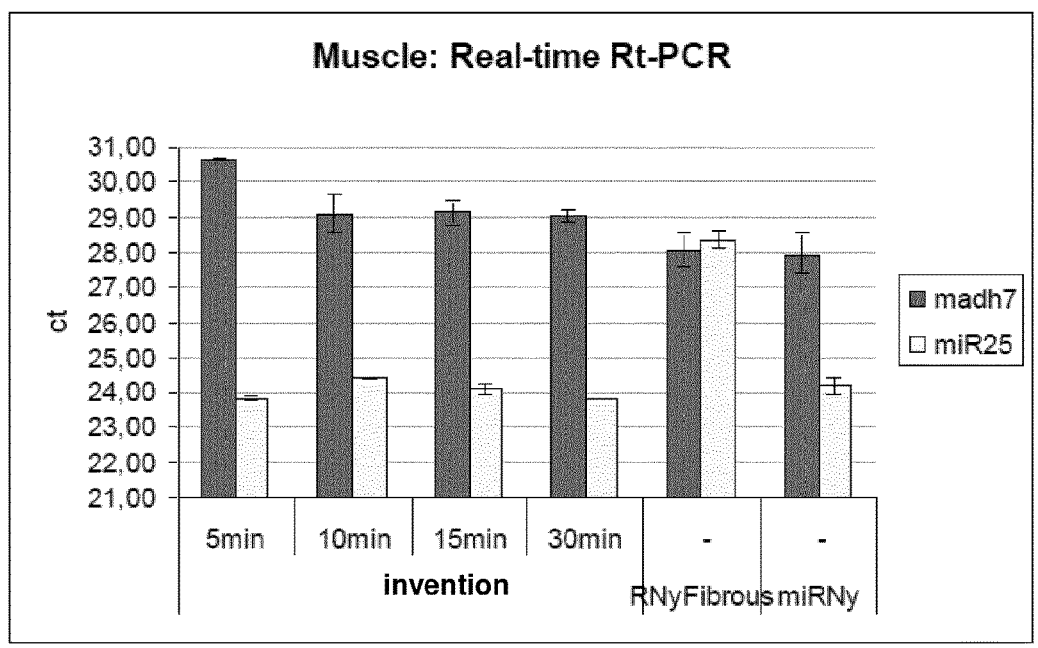

The results for fat (FIG. 18) and muscle (FIG. 19) tissue show that incubation times from 5 to 30 minutes result in no significant differences in the downstream application analysis; the ct values were similar and the yield comparable. However, as an incubation time of 5 minutes showed higher Ct values in the mRNA assay (madh-7) with muscle tissue, it is preferred to use at least 7.5 minutes, more preferably 10 minutes incubation time.

If higher amounts of starting material are used, for example 20 mg of fresh or frozen tissue instead of 10 mg tissue, the proteinase K concentration should be increased.

In most protocols proteinase K digestion is performed with constant shaking at defined temperatures in a thermoshaker. However, not having to use a thermo-shaker for the proteinase K digestion is preferred for the customer and furthermore, also allows to integrate the present protocol into automated systems. Thus, it was investigated whether room temperature (15-25° C). can be used during the proteinase K digest without loss of performance and whether shaking during digestion brought advantages or not. For this purpose, RNA including miRNA was purified from 20 mg RNALater stabilized rat muscle tissue using the protocol according to the present invention wherein the proteinase K digestion after addition of the first amount of alcohol was performed at different temperatures (15° C., 18° C., 20° C., 25° C., 30° C.) and with or without constant shaking at 1.000 rpm. The yield was determined by Nanodrop measurement. The same volume of eluate was used as template in a miRNA Assay miR-25 and an RT-PCR assay with the larger mRNA amplicon madh-7.

The results showed that the RNA yield and Ct values were comparable independently from proteinase K digestion conditions like temperature or shaking (data not shown). Therefore, it is possible to perform the proteolytic digest without shaking at room temperature.

Example 6

RNA Isolation Using On-column DNase Digest and Rebinding Procedure

Figure 20:
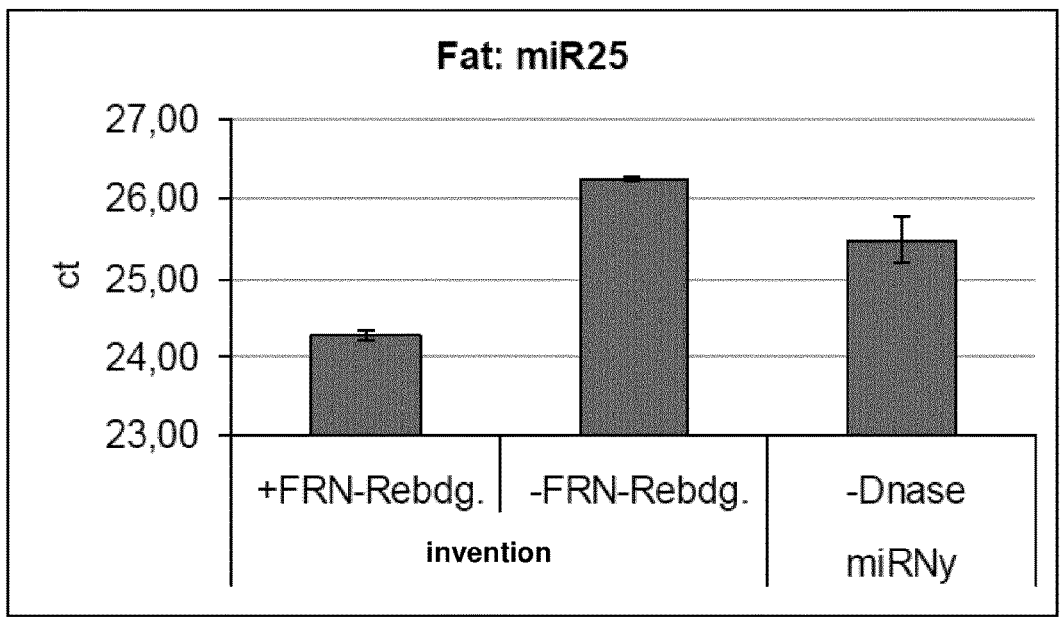
FIGS. 20 to 22: Demonstrates the effect of DNase digestion and rebinding step on miRNA recovery in RNA isolated from different sample types (see example 6). Shown are miRNA assay results.
Figure 21:
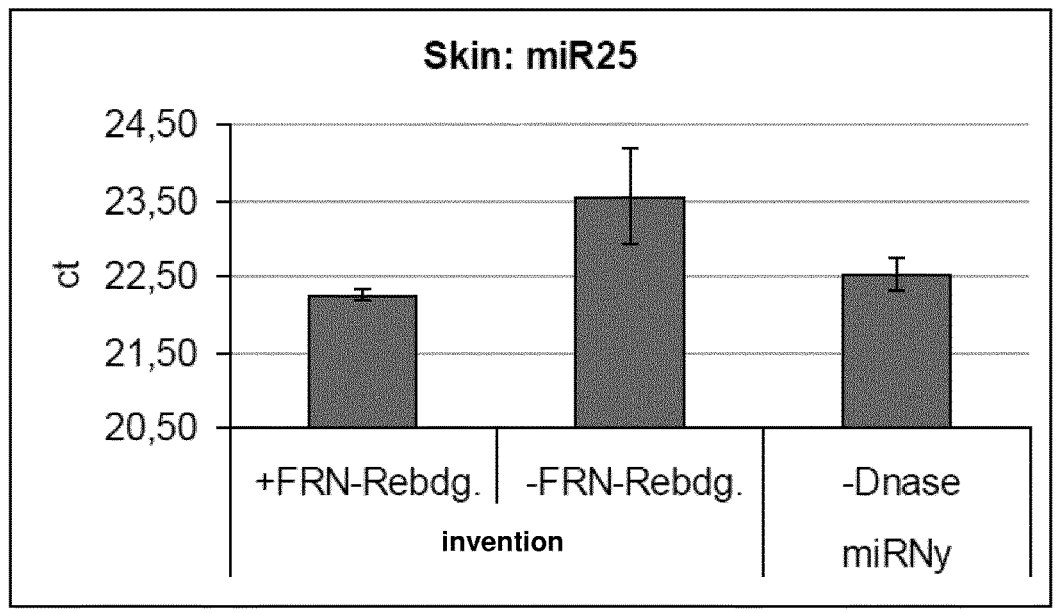
Figure 22:
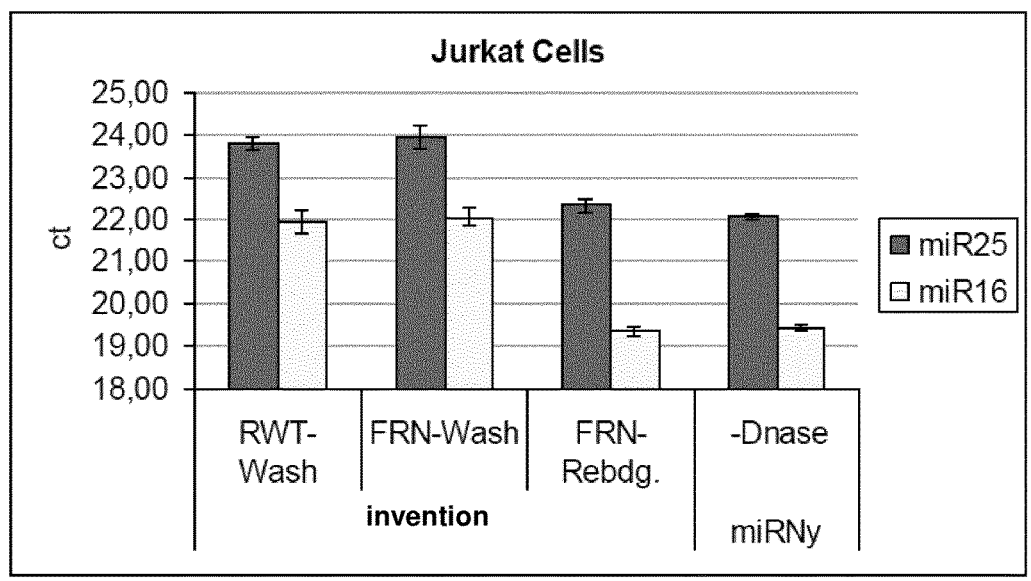

In particular for specific DNA-rich tissues it is favorable to include a DNase digest in the RNA isolation procedure, even if the genomic DNA is removed in advance. Performing a respective DNase digest during RNA isolation allows to remove residual DNA contaminations. However, if performing an on-column DNase digest there is a risk that small RNA gets lost. Therefore, a rebinding step was included in example 6, wherein after the DNase digest, a recovery solution is passed through the column and the flow-through is then collected. The respectively collected flow-through comprises small RNA which might have been released during the DNase digest. The respective collected fraction is then reapplied to the column, in order to rebind the small RNA to the column. The improvement that can be achieved thereby is demonstrated in FIGS. 20-22. Here, the RNA was purified using the teachings according to the present invention from different RNALater stabilized rat tissue and Jurkat cells using the method according to the teachings of the present invention (see in particular example 2), wherein, however, a DNase digest was performed after the RNA was bound to the column. After performing a DNase I digestion, either normal washing steps were performed, or a rebinding step (FRN-rebinding) using a recovery solution as taught herein. The same volume of eluate was used as template in miRNA assay miR-16 and miR-25.The recovery solution used comprised a high concentration of a chaotropic salt, namely 5M of a guanidinium salt.

The results show that the procedure wherein a recovery solution is used results in significantly lower Ct values compared to those protocols, wherein normal washing steps were performed after DNase digestion. The figs. show that it is beneficial to reapply the collected flow-through comprising the recovery solution and potentially escaped small RNA to the column, to ensure that the respectively escaped small RNA species are rebound to the column and therefore are not lost during the purification procedure.

It is preferred to first wash the bound RNA using an appropriate buffer, such as for example a washing buffer comprising alcohol, prior to performing the DNase digest. Thereby it is ensured that the DNase activity is not inhibited due to residual amounts of chaotropic agent and proteinase K comprised in the column. By performing a washing step prior to the DNase treatment it is ensured that the DNA enzyme works at full efficiency and can completely digest any remaining genomic DNA contamination.

Example 7

Isolation of RNA and DNA from Cell Culture

Figure 23:
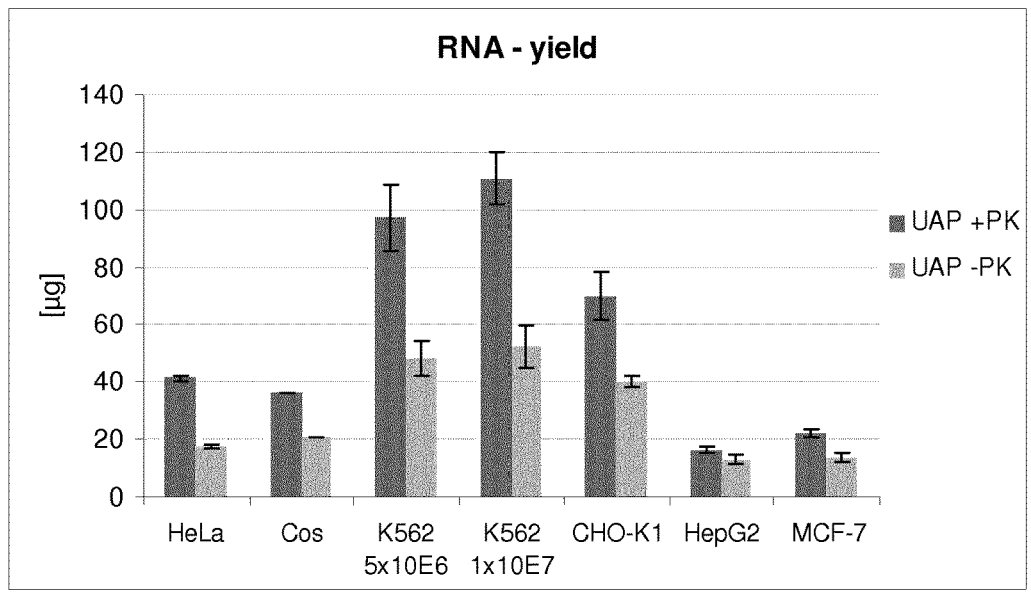
FIG. 23: Isolation of RNA and DNA from cells with or without proteinase K digestion in incubation step c) (see example 7).

RNA and DNA were isolated in parallel, using either the protocol according to the present invention (stepwise addition of alcohol and proteinase K digestion after the first addition of alcohol-UAP+PK) or not including a proteinase K digestion in the isolation procedures and adding alcohol in one step (UAP-PK). The RNA isolation was carried out with or without DNase digestion. The following cell lines were tested: K562 in suspension, Hela cells (adherent), COS-7 (adherent), CHO-K1 (adherent), HEPG-2 (adherent), MCF-7 (adherent). The results are shown in FIG. 23. As can be seen, in all tested cell lines the results were considerably improved when the alcohol is added in a stepwise manner and performing a proteolytic digest during the incubation step after the first amount of alcohol was added. The improved results were also confirmed by performing a real time RT-PCR of the same volume of sample eluates for the mRNA amplicon actin or miRNA miR-16. In all cases, better Ct values were achieved with the protocol according to the present invention (data not shown). The results demonstrate that most cell lines show significantly better performances when isolating the RNA using the method according to the present invention, wherein the alcohol is

29 added stepwise and a proteinase K digestion is performed after adding the first amount of alcohol. Furthermore, it was also found that the DNA yield can be improved when performing a proteolytic digest in a chaotrope/alcohol milieu while the DNA is bound to the solid phase as taught herein.

Example 8

RNA and DNA Isolation from Whole Blood Samples

Whole blood samples stabilized with an anticoagulant (EDTA) were first treated with an erythrocyte lysis buffer, in order to lyse the red blood cells. The white blood cells were collected as pellet and the RNA and DNA was purified from the pellet using the method according to the teachings of the present invention, wherein the alcohol was added in a stepwise manner and a proteolytic digest was performed after the first amount of alcohol was added (UAP+PK). For comparison, the same protocol was performed, however, not including in the RNA isolation the proteolytic digest and not adding the alcohol in a stepwise manner (UAP−PK). The experiment was performed either including an on-column DNase digest or without performing a respective DNase digest. The obtained eluates were analyzed on a 1% formaldehyde gel by applying an equal amount of eluate.

Figure 24:
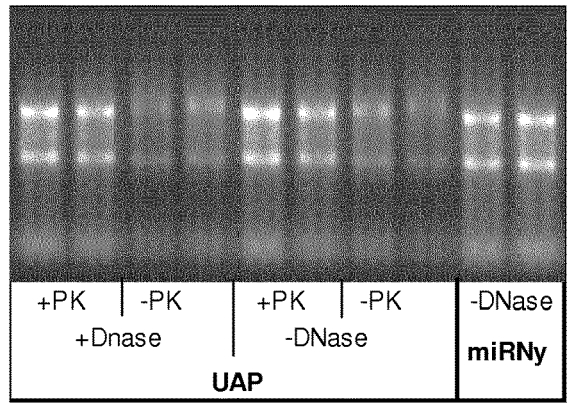
FIG. 24: Isolation of RNA from whole blood sample with or without proteinase K and/or DNase digestion (see example 8). Shown are pictures obtained after gel electrophoresis of an aliquot of the isolated RNA.
Figure 24:
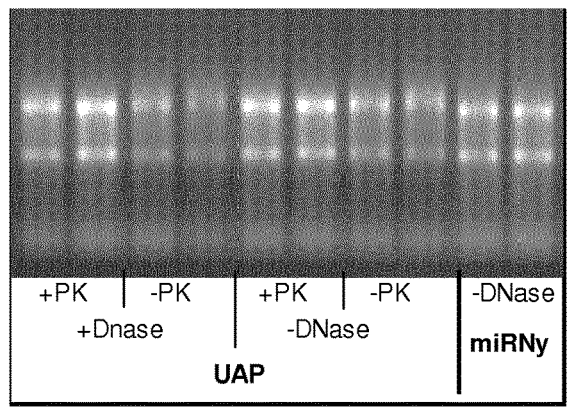

The results obtained for EDTA-stabilized blood from two different donors are shown in FIGS. 24a and 24b. As a control, the miRNeasy protocol (comprising a phenol/chloroform extraction step) was performed. The results show, that the RNA yield could be improved when using the method according to the present invention (see FIGS. 24a and 24b).

Example 9

RNA Isolation from Brain

Figure 25:
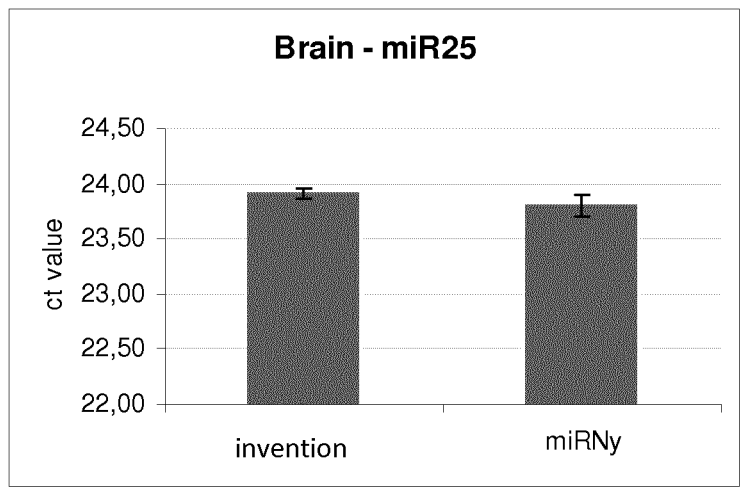
FIG. 25: Shows miRNA assay results obtained with RNA isolated according to example 9.
Figure 25:
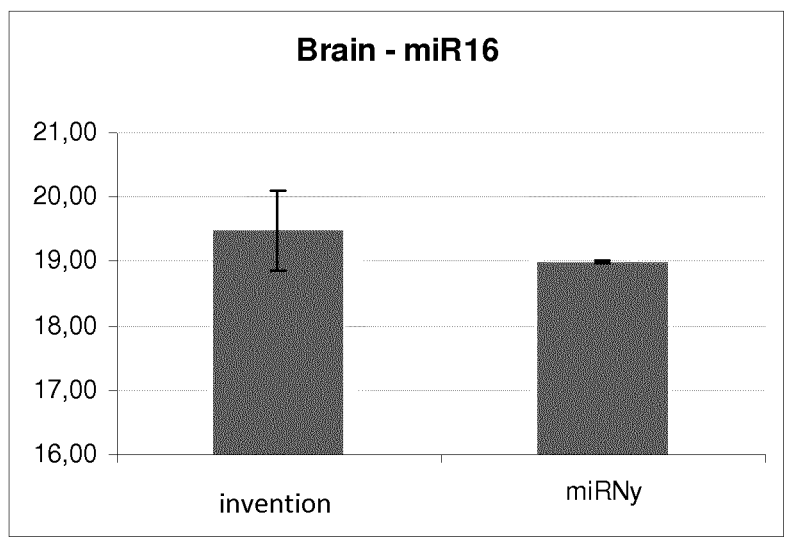

RNA was isolated from brain samples following the protocol described in example 2 with the following modifications. As brain has a very high fat content, a chloroform extraction step as described in example 5 was performed with the DNA depleted flow-through. Additionally, an on-column DNase digest and a subsequent rebinding step as described in example 6 was performed. For comparison, RNA was isolated using the phenol-chloroform based miRNeasy protocol. The same eluate volume was used as template in a quantitative, real-time RT-PCR assay for miRNAs (miR-25 and miRNA 16). The results are shown in FIGS. 25a and 25b and confirm that the isolation results that are achieved with the method according to the present invention even with difficult samples such as brain are comparable to phenol-chloroform based methods.

The invention claimed is:

1. A method for isolating RNA, including small RNA having a length of 200 nt or less, from a sample, comprising the following steps:
    a) providing a composition comprising RNA and a chaotropic agent;
    b) adding alcohol to generate a first mixture;
    c) incubating the first mixture for at least 2 min to generate an incubated first mixture;
    d) adding additional alcohol to the incubated first mixture to generate a second mixture so that the overall alcohol concentration in the second mixture is ≥50%;
    e) binding RNA including small RNA to a nucleic acid binding solid phase, wherein the nucleic acid binding solid phase is contacted with the second mixture in step d), and optionally additionally with one or more selected from the group consisting of (i) the composition in step a), (ii) the first mixture in step b), and (iii) the first incubated mixture in step c);
    f) optionally washing the bound RNA; and
    g) optionally eluting RNA from the solid phase;
    wherein no separation of the nucleic acid binding solid phase, if present at steps b), c) and/or d), and the first mixture, the incubated first mixture, or the second mixture is performed at any of steps b), c) and d),
    wherein the alcohol that is added in step b) and in step d) is selected from methanol, ethanol, propanol, isopropanol, butanol, and mixtures thereof, and
    wherein
        i) the amount of alcohol added in step b) corresponds to approximately 40% to 80% of the overall alcohol concentration that is added for binding in step e); and/or
        ii) an amount of alcohol is added in step b) so that the first mixture comprises the alcohol in a concentration that lies in a range from 25% (v/v) to 45% (v/v).

2. The method according to claim 1, wherein in step c) a proteolytic digest using a proteolytic enzyme is performed.

3. The method according to claim 1, wherein
    an amount of alcohol is added in step b) so that the first mixture comprises the alcohol in a concentration that lies in a range from 25% (v/v) to 45%(v/v).

4. The method according to claim 1, wherein in step c):
    i) incubation occurs at a temperature between 15° C. to 30° C.; and/or
    ii) incubation occurs for at least 2.5 minutes, at least 3 minutes, at least 5 minutes, at least 7.5 minutes, or at least 10 minutes.

5. The method according to claim 2, wherein the first mixture that is incubated in step c) comprises:
    RNA;
    a chaotropic salt in a concentration selected from 1 to 5M, 1.5 to 4.5M, 2 to 4 M and 2.5M to 3.75M;
    a proteolytic enzyme; and
    alcohol in a concentration selected from ≥25%(v/v) and ≤42.5% (v/v).

6. The method according to claim 1, wherein the alcohol that is added in step b) and in step d)
    is isopropanol or ethanol.

7. The method according to claim 1, wherein the composition provided in step a) has been obtained by performing at least the following steps:
    obtaining an RNA containing biological sample;
    lysing the sample;
    optionally homogenising the lysate; and
    optionally clearing the lysate.

8. The method according to claim 1, wherein the composition provided in step a) has been obtained by performing at least the following steps:
    a) 1) obtaining an RNA and DNA containing biological sample;
    a) 2) lysing the sample;
    a) 3) optionally homogenising the lysate;
    a) 4) optionally clearing the lysate; and
    a) 5) removing DNA from the lysate.

9. The method according to claim 8, wherein DNA is removed from the lysate by performing one or more of the following:
    performing a DNase digest in the lysate; and/or
    selectively binding DNA to a nucleic acid binding solid phase and separating the bound DNA from the remaining sample, thereby providing a DNA depleted RNA containing composition for step a).

10. The method according to claim 1, wherein the nucleic acid binding solid phase is:
   i. comprised in a column;
   or
   ii. is provided by particles.

11. The method according to claim 1, wherein in step e) a nucleic acid binding phase comprised in a column is used, and after RNA binding, an on-column DNase digest is performed.

12. The method according to claim 1, wherein magnetic particles are used as nucleic acid binding solid phase, and wherein said method has one or more of the following features:
   i) the magnetic particles are added in one of steps a) to e), and/or
   ii) an RNA and DNA containing sample is lysed in the presence of a chaotropic agent thereby providing an RNA containing composition for step a) of claim 1; steps b) to d) are performed; after step e), RNA and DNA, including small RNA, are bound to the magnetic particles; after binding, one or more washing steps and a DNase digest is performed; after performing the DNase digest, a chaotropic agent and an alcohol are added to rebind RNA that was potentially released during the DNase digest to the magnetic particles; and optionally one or more washing steps are performed and the RNA is eluted from the magnetic particles.

13. The method according to claim 1, wherein said method is for the parallel isolation of RNA and DNA, and wherein said method comprises the following steps:
   obtaining an RNA and DNA containing biological sample;
   lysing the sample wherein lysis involves the use of at least one chaotropic salt;
   optionally homogenising the lysate; and
   optionally clearing the lysate;
   wherein the isolation of the DNA comprises the following steps:
   a) removing DNA from the lysate by selectively binding DNA to a nucleic acid binding solid phase and separating the bound DNA from the remaining sample, thereby providing a DNA depleted RNA containing composition which comprises a chaotropic salt that can be used in step a) of the RNA isolation;
   b) optionally washing the bound DNA;
   c) optionally performing a proteolytic digest while the DNA is bound to the nucleic acid binding solid phase;
   d) optionally washing the bound DNA; and
   e) optionally eluting the bound DNA;
   and wherein the isolation of RNA comprises the following steps:
   a) obtaining the DNA depleted RNA containing composition obtained after step a) of the DNA isolation process, wherein said composition comprises a chaotropic salt;
   b) adding alcohol thereby providing a first mixture which comprises the alcohol in a concentration of ≥25% (v/v) and ≤42.5% (v/v);
   c) incubating the first mixture for at least 2 min in the presence of a proteolytic enzyme;
   d) adding additional alcohol to the first mixture to generate a second mixture so that the overall alcohol concentration in the second mixture is ≥55%;
   e) binding RNA and small RNA contained in the second mixture to a nucleic acid binding solid phase;
   f) optionally washing the bound RNA; and
   g) optionally eluting RNA from the solid phase.

14. The method according to claim 13, wherein in the DNA isolation a proteolytic digest is performed in step c) while the DNA is bound to the nucleic acid binding solid phase, and wherein said proteolytic digest has one or more of the following features:
   i) a proteolytic enzyme is used, and the proteolytic digest occurs in the presence of alcohol and a chaotropic salt;
   ii) for performing the proteolytic digest, a proteolytic composition is added which comprises a proteolytic enzyme, alcohol and a chaotropic salt;
   iii) the proteolytic digest is performed at a temperature from 15° C. to 30° C.; and/or
   iv) the proteolytic digest occurs for a time period selected from 3 min to 45 min or 5 min to 30 min.

15. The method according to claim 13, wherein in the RNA isolation a DNase digest is performed after the RNA was bound to the nucleic acid binding solid phase in step e) and wherein small RNA potentially released during the DNase digest is rebound to the solid phase.

16. The method according to claim 1, having one or more of the following characteristics:
   i) the nucleic acid binding solid phase is a silicon containing material;
   ii) the sample is a cell containing sample;
   iii) the sample is a tissue sample; and/or
   iv) the sample is a fibrous tissue sample.

17. The method of claim 3, wherein
   i) the amount of alcohol added in step b) corresponds to approximately 55% to 65% of the overall alcohol concentration that is added for binding in step e); and/or
   ii) the resulting first mixture comprises the alcohol in a concentration that lies in a range from 30% to 40% (v/v).

18. The method of claim 3, wherein an amount of alcohol is added in step b) so that the resulting first mixture comprises the alcohol in a concentration that lies in a range from 32.5% to 38% (v/v).

19. The method of claim 5, wherein the proteolytic enzyme is proteinase K.

20. The method of claim 5, wherein the alcohol is in a concentration from 32.5% to 40% (v/v).

21. The method of claim 7, wherein lysing the sample involves the use of at least one chaotropic salt.

22. The method of claim 8, wherein lysing the sample involves the use of at least one chaotropic salt.

23. The method of claim 10, wherein the nucleic acid binding solid phase is magnetic particles.

24. The method of claim 10, wherein the nucleic acid binding solid phase is a silicon containing material.

25. The method of claim 24, wherein the silicon containing material is silica, a polysilicic acid material, a borosilicate, a silicate or an inorganic glass.

26. The method of claim 11, wherein after the DNase digest, the following steps are performed:
   collecting small RNA which might have been released from the nucleic acid binding solid phase during the DNase digest as flow through; and
   containing the flow through which comprises small RNA mixed with a recovery solution with a nucleic acid binding solid phase for binding the contained small RNA to the nucleic acid binding solid phase.

27. The method of claim 2, wherein the proteolysis enzyme is added prior to step b).

\* \* \* \* \*